(12) United States Patent
Joubert et al.

(10) Patent No.: US 10,174,065 B2
(45) Date of Patent: *Jan. 8, 2019

(54) ANTIDIABETIC ENOLIC GLUCOSIDE OF PHENYLPYRUVIC ACID

(71) Applicant: ZADEC APS, Hoersholm (DK)

(72) Inventors: Elizabeth Joubert, Somerset West (ZA); Stephen John Fey, Blommenslyst (DK); Johan Louw, Durbanville (ZA); Trond Ulven, Copenhagen K (DK); Rahul Tyagi, Odense C (DK)

(73) Assignee: ZADEC APS, Hoersholm (DK)

( * ) Notice: Subject to any disclaimer, the term of this patent is extended or adjusted under 35 U.S.C. 154(b) by 164 days.

This patent is subject to a terminal disclaimer.

(21) Appl. No.: 14/945,109

(22) Filed: Nov. 18, 2015

(65) Prior Publication Data

US 2016/0083411 A1  Mar. 24, 2016

Related U.S. Application Data

(62) Division of application No. 13/878,158, filed as application No. PCT/EP2010/065052 on Oct. 7, 2010, now Pat. No. 9,221,860.

(51) Int. Cl.
| | | |
|---|---|---|
| *C07H 15/18* | (2006.01) | |
| *C07H 15/26* | (2006.01) | |
| *C07H 15/203* | (2006.01) | |

(52) U.S. Cl.
CPC ........... *C07H 15/203* (2013.01); *C07H 15/18* (2013.01); *C07H 15/26* (2013.01)

(58) Field of Classification Search
None
See application file for complete search history.

(56) References Cited

FOREIGN PATENT DOCUMENTS

| CN | 1679706 | 10/2005 |
|---|---|---|
| JP | 8-283121 | 10/1996 |
| JP | 2003-84391 | 3/2003 |
| JP | 2003-121964 | 4/2003 |
| JP | 2006-316020 | 11/2006 |
| JP | 2008-156264 | 7/2008 |
| WO | WO 2008/110551 | 9/2008 |

OTHER PUBLICATIONS

Bastin, R. J. et al., Organic Process Research & Development, "Salt Selection and Optimisation Procedures for Pharmaceutical New Chemical Entities", 2000, vol. 4, pp. 427-435.*
CAPLUS record of Tsai et al., Accession No. 2009:31436; RN 180161-92-6, one page.*
Kato, E. et al., Tetrahedron, "Synthetic inhibitor of leaf-closure that reveals the biological importance of leaf-movement for the survival of leguminous plants", 2003, vol. 59, pp. 5909-5917.*
Tsai, T.-H. et al., Chem. Pharm. Bull., "Phenolic Glycosides and Pyrrolidine Alkaloids from Codonopsis tangshen", 2008, vol. 56, No. 11, pp. 1546-1550.*
Berthiol et al., "Heck Reaction of Protected Alk-1-en-3-ol, -4-ols, -5-ol or -6-ol with Aryl Bromides Catalysed by a Palladium Complex Derived from a Tetraphosphine", *Synthesis*, No. 9, 2006, pp. 1518-1536.
Guzman et al., "Synthesis and cytotoxic evaluation of some structural fragments of epothilone A", XP-002629142.
Ikemoto et al., "Glucosides for alleviation of skin irritation caused by lower alcohols, and aqueous alcohol solutions containing the glucosides", XP-002629167.
International Search Report from International Application No. PCT/EP2010/065052 dated Mar. 31, 2011.
Liu et al., "A Chinese medicinal composition from Panax notoginseng and Rhodiola sacra for treating cardiovascular and cerebrovascular diseases, and its preparation method", XP-002629145.
Marais et al., "The Occurrence of Phenylpyruvic Acid in Woody Plants: Biosynthetic Significance", *Tetrahedron Letters*, vol. 37, No. 32, 1996, pp. 5763-5764.
Sugimoto et al., "Biomimetic Synthesis of a Leaf-opening Factor, Potassium Isolespedezate by Direct Formation of Enol-glycoside", *Chemistry Letters*, vol. 33, No. 8, 2004, pp. 976-977.
Marais et al., "Occurrence of Phenylpyruvic Acid in Woody Plants: Biosynthetic Significance and Synthesis of an Enolic glucoside Derivative", *Journal of the Chemical Society*, Perkin Transactions 1, Issue 24, 1996, pp. 2915-2918.

* cited by examiner

*Primary Examiner* — Layla D Berry
*Assistant Examiner* — Bahar Craigo
(74) *Attorney, Agent, or Firm* — Merchant & Gould P.C.

(57) ABSTRACT

There is provided an antidiabetic enolic glucoside of phenylpyruvic acid and derivatives thereof for use as medicaments, especially normoglycemic agents, i.e. for lowering blood glucose levels to normal levels in mammals that are obese, pre-diabetic or have diabetes, obesity and/or syndrome X. Hence the compounds of the present invention help to manage blood sugar levels, i.e. helping the body by balancing the blood sugar levels; helping to keep balanced blood glucose levels, particularly in humans with diabetes; aiding by enhancing the glucose uptake by the cells and by reducing sugar levels, thus improving or restoring the glucose tolerance; optimizing the glycemic response; normalizing the glucose tolerance.

1 Claim, 2 Drawing Sheets

ANTIDIABETIC ENOLIC GLUCOSIDE OF PHENYLPYRUVIC ACID

This application is a Continuation Application of U.S. patent application Ser. No. 13/878,158, filed 24 Jun. 2013, which is a National Stage Application of PCT/EP2010/065052, filed 7 Oct. 2010, which application is incorporated herein by reference. To the extent appropriate, a claim of priority is made to the above disclosed application.

FIELD OF THE INVENTION

The present invention relates to compounds for use as medicaments, especially normoglycemic agents, i.e. for lowering blood glucose levels to normal levels in mammals that are obese, pre-diabetic or have diabetes, obesity and/or syndrome X.

BACKGROUND OF THE INVENTION

Diabetes mellitus defines a complex of metabolic diseases derived from multiple causative factors and is characterized by impaired glucose metabolism, usually associated with impaired protein and fat metabolism. This results in elevated fasting and postprandial serum glucose levels that leads to complications if left untreated.

Four different forms of diabetes mellitus are known, (1) type 1 diabetes mellitus (T1D), (2) type 2 diabetes mellitus (T2D), (3) the so-called gestational diabetes mellitus, which begins or is recognized for the first time during pregnancy, and (4) some other forms which are mainly based on genetic defects. The two major forms of diabetes mellitus are the type 1 and type 2 diabetes mellitus, of which T2D is the most prevailing form.

There are many theories for explaining the impairment of insulin production by the pancreas that leads to type 1 diabetic condition. Reference is made to two papers. The first is entitled "Possible toxic effects of normal and diabetic patient serum on pancreatic B-cells" by Lernmark A, Sehlin J, Täljedal I B, Kromann H, Nerup J. published in Diabetologia. 1978 Jan. 14; 14(1):25-31. The second is "Autoimmune Imbalance and Double Negative T Cells Associated with Resistant, Prone and Diabetic Animals", Hosszufalusi, N., Chan, E., Granger, G., and Charles, M.; J Autoimmun, 5: 305-18 (1992). These papers show that inflammation of the pancreatic Islets interrupts insulin production. Specifically, the insulin producing beta cells in the pancreatic islets are destroyed by immune attack. Such beta cell destruction is recognized as being due to attack by several types of immune cells including NK (natural killer) cells and double negative T-Lymphocytes. The identification of antibodies against certain proteins (e.g. GAD65, insulin etc.) is used as one of the diagnostic parameters to detect T1D. Even so this autoimmune attack is considered a secondary event following changes in the islets themselves and these changes probably set in many years before the clinical onset of diabetes.

T2D is associated with hyperglycemia, hypercholesterolemia and hyperlipidemia. The insensitivity to insulin in T2D leads to a decrease in glucose utilization by the liver, muscle and the adipose tissue and to an increased blood glucose level. Uncontrolled hyperglycemia is associated with the dysfunction and failure of various organs such as the eyes, heart, blood vessels, kidney and nerves thus leading to increased and premature mortality due to an increased risk for microvascular and macrovascular diseases, including nephropathy, neuropathy, retinopathy, ulceration of the legs and feet, fatty liver disease, hypertension, cardiovascular diseases, and cerebrovascular diseases (stroke), the so-called diabetic complications. Recent evidence showed that tight glycemic control is a major factor in the prevention of these complications in T2D. Therefore, optimal glycemic control by drugs or therapeutic regimens is an important approach for the treatment of T2D.

T2D is the form of diabetes mellitus which occurs predominantly in adults, in whom adequate production of insulin is available for use in the early stage of the diseases, yet a defect exists in insulin action especially insulin-mediated utilization and metabolism of glucose in peripheral tissues. The changes in various tissues associated with T2D also exist many years before clinical symptoms are detected.

T2D is diagnosed by raised levels of plasma glucose. Following diagnosis of diabetes by raised blood glucose levels, therapies such as diet and exercise and/or available medication can result in a temporary improvement in plasma glucose levels but cannot halt the progression of the disease. The rate of failure of these therapies is associated with the rate of continuing beta-cell decline.

The incidence of T2D is increasing worldwide. Although genetic factors may play a role, the increase is normally attributed to life-style changes such as the adoption of a Western diet, high in fat, leads to obesity which can be a factor contributing to the increase of this disease. Life-style factors, such as increased fat intake and reduced exercise, have been shown to be associated with obesity and insulin resistance. In rats, high fat feeding induces a state of insulin resistance associated with diminished insulin-stimulated glycolysis and glycogen synthesis. This disease is a result of the peripheral insulin-responsive tissues, such as muscle and adipose tissue, displaying a significant decrease in response to insulin resulting in an increase in circulating glucose and fatty acids in the blood. The low response to insulin results in a decrease in glycolysis which in turn initiates gluconeogenesis and glycogenolysis in the liver, both of which are "switched off" by insulin under normal conditions.

Pancreatic cells are able to cope with the initial insulin resistant phase by producing an excess of insulin and increasing the amount of insulin secreted. The resulting hyperinsulinaemia to maintain normoglycaemia eventually brings about cell dysfunction leading to full blown diabetes. It is evident that T2D is dependent on insults occurring both at peripheral as well as the cell level.

Diabetes is considered to be insidious, since there is no cure known at this time. Various treatments, however, have been used to ameliorate diabetes.

At present, T1D patients are treated with insulin. Unfortunately, the use of insulin currently requires multiple daily doses, normally administered by self-injection, with determination of the proper dosage of insulin requiring frequent estimations of the sugar in urine or blood, performed either by the patient or the administering physician. The unintended administration of an excess dose of insulin can result in hypoglycemia, with adverse effects ranging from mild abnormalities in blood glucose to coma, or even death.

Therapy of T2D initially involves dietary and lifestyle changes (including increased exercise). When these measures fail to maintain adequate glycemic control, the patients are treated with oral hypoglycemic agents and/or exogenous insulin. The current oral pharmacological agents for the treatment of T2D include those that potentiate insulin secretion (sulphonylurea agents), those that improve the action of insulin in the liver (biguanide agents), insulin sensitizing agents (thiazolidinediones) and agents which act to inhibit the uptake of glucose in the gastrointestinal tract (α-glucosidase inhibitors). Biguanides, such as metformin, became available for treatment of type 2 diabetes in the late 1950s, and have been effective hypoglycaemic agents ever since. As an insulin sensitizer, metformin acts predominantly on the liver, where it suppresses glucose release. Metformin has also been shown to inhibit the enzymatic activity of complex I of the respiratory chain and thereby impairs both mitochondrial function and cell respiration, and in so doing decreasing the ATP/ADP ratio which activates AMP activated protein kinases causing catabolic responses on the short term and insulin sensitization on the long term. This drug has been proven effective in both monotherapy and in combination with sulfonylureas or insulin.

However, currently available agents generally fail to maintain adequate glycemic control in the long term due to progressive deterioration in hyperglycemia, resulting from progressive loss of pancreatic cell function. The proportion of patients able to maintain target glycemic levels decreases markedly overtime necessitating the administration of additional/alternative pharmacological agents. Furthermore, the drugs may have unwanted side effects and are associated with high primary and secondary failure rates.

Therefore, there is a need for compounds with minimal side effects for the prevention, control and/or treatment of diabetes mellitus and for the prevention of the physical complications associated with it as mentioned above. Many patients are interested in alternative therapies which could minimize the side effects associated with high-dose of drugs and yield additive clinical benefits. Diabetes mellitus is a progressive and chronic disease, which usually is not recognized until significant damage has occurred to the pancreatic cells responsible for producing insulin and to the cardiovascular system. Therefore, there is also an increasing interest in the development of novel treatments of diabetes mellitus in people at risk especially in elderly persons, but also in obese children, (who are at high risk for developing T1D or T2D). Since T2D is often associated with symptoms from syndrome X ("metabolic syndrome"), such as hypertriglyceridemia or dyslipidemia, the compounds according to the present invention are also useful for the treatment or prevention of syndrome X.

There has been a renewed focus on pancreatic islet-based insulin secretion that is controlled by glucose-dependent insulin secretion. This approach has the potential for stabilization and restoration of beta-cell function. In this regard, several orphan G-protein coupled receptors (GPCR's) have recently been identified that are preferentially expressed in the beta-cell and are implicated in glucose dependent insulin secretion (GDIS). GPR119 is a cell-surface GPCR that is highly expressed in human (and rodent) islets as well as in insulin-secreting cell lines. A naturally-occurring long-chain fatty acid amide, oleoylethanolamide (OEA) and several long chain saturated and unsaturated lysophospholipids such as 1-palmitoyl-lysophosphatidylcholine and 2-oleoyl-lysophosphatidylcholine, as well as synthetic compounds, have recently been identified as ligands for GPR119. Acute administration of a synthetic small molecule GPR119 agonist to rats reduces 24 h cumulative food intake without significantly altering locomotor activity and in chronic studies, reduces cumulative food intake and body weight indicating that GPR119 agonists may be effective anti-obesity agents. Synthetic GPR119 agonists also augment the release of insulin from isolated static mouse islets only under conditions of elevated glucose and improve glucose tolerance in diabetic mice and diet-induced obese mice without causing hypoglycemia. GPR119 agonists therefore have the potential to function as anti-hyperglycemic agents that produce weight loss.

There are several potential advantages of GPR119 as a potential target for the treatment of type 2 diabetes and obesity. First, since GPR119-mediated insulin secretion is glucose dependent, there is little or no risk of hypoglycemia. Second, the weight loss efficacy of GPR119 agonists should contribute to antihyperglycemic efficacy in diabetic and prediabetic obese subjects, and activation of GPR119 may allow for the simultaneous treatment of the common co-morbidities of obesity and impaired glucose tolerance/diabetes. Third, the limited tissue distribution of GPR119 in humans (mainly in islets and the GI tract) suggests that there would be less chance for side effects associated with GPR119 activity in other tissues. Fourth, GPR119 agonists may have the potential to restore or preserve islet function since GPR119 agonists increase GLP-1 levels. GLP-1 is an incretin hormone that effects GDIS and exerts anti-apoptotic and proliferative effects on islets. A protective effect on islets upon GPR119 agonism would be highly advantageous, because long term diabetes therapy often leads to the gradual diminution of islet activity, such that after extended periods of treatment with multiple oral antihyperglycemic agents, it is often necessary to treat type 2 diabetic patients with daily insulin injections. By restoring or preserving islet function, GPR119 agonists may delay or prevent the diminution and loss of islet function in a type 2 diabetic patient.

SUMMARY OF THE INVENTION

The present invention relates to a compound of formula I or a physiologically acceptable salts thereof:

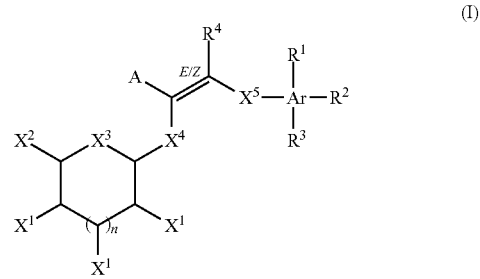

wherein,

Ar is an aromatic or heteroaromatic monocyclic or fused bicyclic or tricyclic system;

n is 0, 1 or 2;

$R^1$, $R^2$, $R^3$, and $R^4$ are independently selected from the group consisting of hydrogen, fluorine, chlorine, bromine, iodine, aryl, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperizin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano, and nitro, $X^1$ is independently selected from the group consisting of —OH, —$CH_2OR^5$, H, —$OR^5$, and —$C(O)R^5$;

$X^2$ is selected from the group consisting of —OH, —$CH_2OR^5$, H, —$OR^5$, and —$C(O)R^5$;

$X^3$ is independently selected from the group consisting of —O—, and —$CH(X^1)$—;

$X^4$ is selected from the group consisting of —O— and (—$CH_2)_m$—;

$X^5$=—O— or (—$CH_2)_m$—;

m is 0, 1, 2 or 3;

A is selected from the group consisting of —$CO_2H$, —$CO_2R^5$, —$SO_3H$; —$SO_2HNR^5$; —$PO(OH)_2$; —CONH$(CO)R^5$; —CONH(CO)H, —$CONHSO_2R^5$; —CONHCN; and

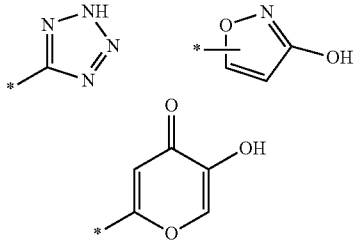

where the bond marked * is attached to the ethylene; and $R^5$ is selected form group consisting of $C_1$-$C_6$ straight or branched chain alkyl, $C_2$-$C_6$ straight or branched chain alkenyl or alkynyl, aryl, aralkyl, heteroaryl, carbocycle, and heterocycle;

with the proviso that:

$X^2$ is different from —OH, when $X^3$ is —O— and at least one $X^1$ is OH;

If $R^1$, $R^2$, $R^3$, and $R^4$ are —H, A is not —$CO_2H$ or —$CO_2R^5$, when $X^1$ is —OH, $X^3$ and $X^4$ is —O—, $X^2$ is —$CH_2OH$, n is 1, and $X^5$ is (—$CH_2)_m$—, where m is 0; and $R^1$, $R^2$ or $R^3$ is not in para position relative to $X^5$ if $R^1$, $R^2$ or $R^3$ is selected from $C_{1-6}$-alkyloxy, $C_{3-10}$-cycloalkyloxy, $C_{5-10}$-cycloalkenyloxy, aryloxy, and hydroxy.

The compounds of the present invention are particularly useful for the treatment of T1D, T2D, obesity and/or syndrome X. The present invention is also directed to dietary and pharmaceutical compositions containing these compounds and to a method for the treatment of T1D, T2D, obesity and/or syndrome X in animals including humans, said method comprising the step of administering an effective dose of a compound of the formula I to animals including humans which are in need thereof. Without being bound by a specific mode of action it is likely that a significant part of the therapeutic effect of the compounds of the present invention may be ascribed to their GPR119 agonism. Hence, the present invention is also directed to the compounds of the present invention as agonists of GPR119.

In the context of this invention "treatment" also encompasses co-treatment as well as prevention, and control.

Animals in the context of the present invention may be mammals including humans. Preferred examples of mammals beside humans are dogs, cats, guinea pigs, (jack) rabbits, hares, ferrets, horses, and ruminants (cattle, sheep and goats).

The present inventors have found that compounds of the formula I, wherein

Ar is benzene;

n=1;

$R^1$, $R^2$, $R^3$, and $R^4$ are independently selected from the group consisting of hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperizin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano, and nitro, A is selected from the group consisting of —$CO_2H$, —$CO_2R^5$, —$SO_3H$; —$SO_2HNR^5$; —$PO(OR^5)_2$; —CN; —$OR^5$; —$NHCOR^5$; —$CONZ(R^5)$; —$CONH(CO)R^5$; —$CONHSO_2R^5$; —$COHNSO_2R^5$; —$CONR^5CN$; and

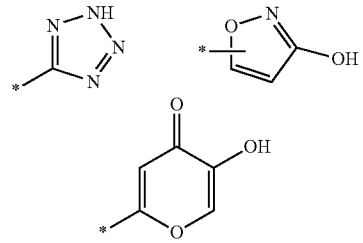

where the bond marked * is attached to the ethylene;

$R^5$ is selected form group consisting of $C_1$-$C_6$ straight or branched chain alkyl, $C_2$-$C_6$ straight or branched chain alkenyl or alkynyl, aryl, aralkyl, heteroaryl, carbocycle, and heterocycle;

$X^1$ is —OH;

$X^2$ is —$CH_2OH$, —OH, H, OMe, and OAc;

$X^3$ is —O—;

$X^4$ is —O—;

$X^5$ is (—$CH_2)_m$—;

and/or m=1, excluding compounds, where:

$X^2$ is different from —OH, when $X^3$ is —O— and at least one $X^1$ is OH;

If $R^1$, $R^2$, $R^3$, and $R^4$ are H, A is not —$CO_2H$ or —$CO_2R^5$, when $X^1$ is —OH, $X^3$ and $X^4$ is —O—, $X^2$ is —$CH_2OH$, n is 1, and $X^5$ is (—$CH_2)_m$—, where m is 0; and $R^1$, $R^2$ or $R^3$ is not in para position relative to $X^5$ if $R^1$, $R^2$ or $R^3$ is selected from $C_{1-6}$-alkyloxy, $C_{3-10}$-cycloalkyloxy, $C_{5-10}$-cycloalkenyloxy, aryloxy, and hydroxy.

are particularly effective agents in the prevention, control and/or treatment of non-autoimmune T2D, obesity and/or syndrome X, in animals including humans, especially in mammals including humans.

Most preferred compounds are those of formula (I), wherein
A is —COOH;
n=1;
Ar is benzene;
$R^1$, $R^2$, $R^3$, and $R^4$ are independently selected from the group consisting of hydrogen, fluorine, chlorine, bromine, iodine, hydroxy, cyano, and nitro, preferably hydrogen;
$X^1$ is —OH;
$X^2$ is —CH$_2$OH;
$X^3$ is —O—;
$X^4$ is —O—;
$X^5$ is (—CH$_2$)$_m$—;
and/or
m=1.

Additionally the present invention relates to a compound of formula II for use as a medicament:

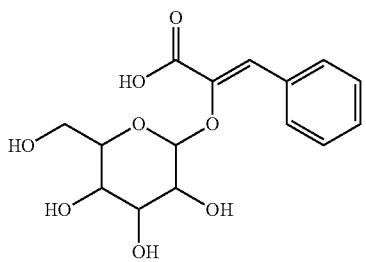

(II)

In a preferred embodiment the present invention relates to an optical isomer of formula II, namely the compound of formula III for use as a medicament

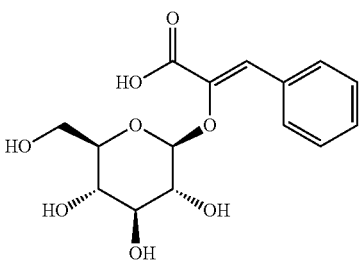

(III)

When reference is made to the compound of formula (II), the isomer of formula (III) is the most preferred optical isomer. Concerning further isomers of the Z-form of compound (II) or (III) is preferred, however, the E-form is also active.

Compound (II) and (III) of the present invention is particularly useful for the treatment of T1D, T2D, obesity and/or syndrome X. The present invention is also directed to dietary and pharmaceutical compositions containing this compound and to a method for the treatment of T1D, T2D, obesity and/or syndrome X in animals including humans, said method comprising the step of administering an effective dose of a compound of the formula II to animals including humans which are in need thereof.

In the context of this invention "treatment" also encompasses co-treatment as well as prevention, and control.

The present invention is also directed to a compound of formula IV for use as a medicament:

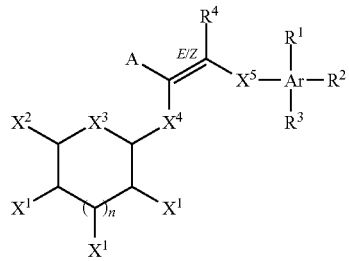

(IV)

wherein,
Ar is an aromatic or heteroaromatic monocyclic or fused bicyclic or tricyclic system;
n is 0, 1 or 2;
$R^1$, $R^2$, $R^3$, and $R^4$ are independently selected from the group consisting of hydrogen, fluorine, chlorine, bromine, iodine, aryl, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperizin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano, and nitro,
$X^1$ is independently selected from the group consisting of —OH, —CH$_2$OR$^5$, H, —OR$^5$, and —C(O)R$^5$;
$X^2$ is selected from the group consisting of —CH$_2$OH, —OH, —CH$_2$OR$^5$, H, —OR$^5$, and —C(O)R$^5$;
$X^3$ is independently selected from the group consisting of —O—, and —CH(X$^1$)—;
$X^4$ is selected from the group consisting of —O— and (—CH$_2$)$_m$—;
$X^5$=—O— or (—CH$_2$)$_m$—;
m is 0, 1, 2 or 3;
A is selected from the group consisting of —CO$_2$H, —CO$_2$R$^5$, —SO$_3$H; —SO$_2$HNR$^5$; —PO(OH)$_2$; —CONH(CO)R$^5$; —CONH(CO)H, —CONHSO$_2$R$^5$; —CONHCN; and

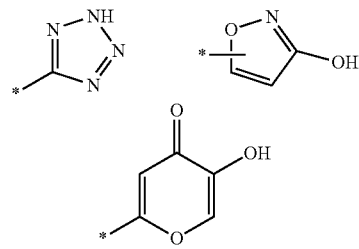

where the bond marked * is attached to the ethylene; and
$R^5$ is selected form group consisting of $C_1$-$C_6$ straight or branched chain alkyl, $C_2$-$C_6$ straight or branched chain alkenyl or alkynyl, aryl, aralkyl, heteroaryl, carbocycle, and heterocycle;

with the proviso that $X^2$ is different from —OH when $X^3$ is —O—; and at least one $X^1$ is OH.

The present inventors have found that compounds of the formula (IV), wherein

Ar is benzene;

n=1;

$R^1$, $R^2$, $R^3$, and $R^4$ are independently selected from the group consisting of hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperizin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano, and nitro, A is selected from the group consisting of —$CO_2H$, —$CO_2R^5$, —$SO_3H$; —$SO_2HNR^5$; —$PO(OR^5)_2$; —CN; —$OR^5$; —$NHCOR^5$; —$CONZ(R^5)$; —CONH(CO)$R^5$; —$CONHSO_2R^5$; —$COHNSO_2R^5$; —$CONR^5CN$; and

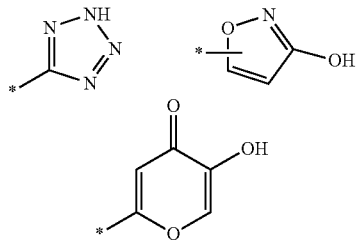

where the bond marked * is attached to the ethylene;

$R^5$ is selected form group consisting of $C_1$-$C_6$ straight or branched chain alkyl, $C_2$-$C_6$ straight or branched chain alkenyl or alkynyl, aryl, aralkyl, heteroaryl, carbocycle, and heterocycle;

$X^1$ is —OH;

$X^2$ is —$CH_2OH$, —OH, H, OMe, and OAc;

$X^3$ is —O—;

$X^4$ is —O—;

$X^5$ is (—$CH_2$)$_m$—;

and/or m=1, are particularly effective agents in the prevention, control and/or treatment of non-autoimmune T2D, obesity and/or syndrome X, in animals including humans, especially in mammals including humans.

Most preferred compounds are those of formula (IV), wherein

A is —COOH;

n=1;

Ar is benzene;

$R^1$, $R^2$, $R^3$, and $R^4$ are independently selected from the group consisting of hydrogen, fluorine, chlorine, bromine, iodine, hydroxy, cyano, and nitro, preferably hydrogen;

$X^1$ is —OH;

$X^2$ is —$CH_2OH$;

$X^3$ is —O—;

$X^4$ is —O—;

$X^5$ is (—$CH_2$)$_m$—;

and/or m=1.

The present invention is also directed to the use of the compounds of the formulas I-IV as defined above for helping to manage blood sugar levels, i.e. helping the body by balancing the blood sugar levels; helping to keep balanced blood glucose levels, particularly in humans with diabetes; aiding by enhancing the glucose uptake by the cells and by reducing sugar levels, thus improving or restoring the glucose tolerance; lowering the blood glucose level; optimizing the glycemic response; normalizing the glucose tolerance; i.e. the compounds of the formula I may be α-glucosidase inhibitors, hyperglycemia treating and/or controlling agents and blood glucose lowering agents; and amelioration of T1D;

reducing sweetness cravings;

reducing appetite;

preserving or improving the pancreatic β-cell function, thus promoting a healthy pancreatic function; i.e. the compounds of the formula I are pancreatic β-cell function improvers;

treating or controlling the insulin sensitivity by e.g. helping to restore/enhance the insulin sensitivity; i.e. the compounds of the formula I may be insulin sensitizing agents;

delaying, preventing or controlling non-autoimmune T2D and thus preventing also the diabetes accompanying disorders/complications such as the ones mentioned above, i.e. the compounds of the formula I may be T2D preventing agents.

The compounds of the present invention are particularly intended for the prevention of non-autoimmune T2D in those individuals in high risk to develop this disease, such as individuals with pre-diabetes, impaired glucose tolerance (IGT), or obesity.

This invention also relates to pharmaceutical compositions, containing at least one compound of formula I-IV or a physiologically acceptable salt thereof, with one or more inert carriers and/or diluents.

This invention also relates to the use of at least one compound of formula I-IV or one of the physiologically acceptable salts of such a compound for preparing a pharmaceutical composition which is suitable for the treatment or prevention of diseases or conditions, such as diabetes.

This invention also relates to the use of at least one compound of formula I-IV for preparing a pharmaceutical composition which is suitable for the treatment of metabolic disorders.

Compounds of formula I-IV are particularly suitable for the prevention or treatment of diseases, particularly metabolic disorders, or conditions such as T1D and T2D, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds of formula I-IV, including the physiologically acceptable salts thereof, are suitable for the prevention or treatment of diabetes, particularly T1D and T2D, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. For a skilled practitioner this would depend on inter alia efficiency of absorption, rate of metabolism, and excretion. Additionally, the gut environment may influence the uptake and stability of the compounds of the invention. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, solutions, suspensions or suppositories.

The use of the compound of formula I-IV, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient one after the other within a period of less than or equal to 12 hours, but particularly less than or equal to 6 hours.

Consequently, in another aspect, this invention relates to a pharmaceutical composition which comprises a compound of formula I-IV or a physiologically acceptable salt of such a compound and at least one of the active substances described above as combination partners, optionally together with one or more inert carriers and/or diluents.

An aspect of the invention is a compound of the invention for use in the treatment (including prophylaxis) of diseases and conditions mediated through GPR119.

An aspect of the invention is a compound of the invention for use in the treatment (including prophylaxis) of metabolic disorders or conditions, such as diabetes and/or obesity.

An aspect of the invention is the use a compound of the invention in the manufacture of a medicament for use in the treatment (including prophylaxis) of metabolic disorders or conditions, such as diabetes and/or obesity.

An aspect of the invention is a method for the treatment (including prophylaxis) of metabolic disorders or conditions, such as diabetes or obesity, comprising the administration of a compound of the invention.

One embodiment of the invention is a method for increasing GLP-1 secretion in a glucose independent and dependent manner through the administration of a GPR119 agonist, such as a compound of the invention.

One embodiment of the invention is a method for reducing food intake through the administration of a GPR119 agonist, such as a compound of the invention.

DETAILED DESCRIPTION OF THE INVENTION

Figure 1:
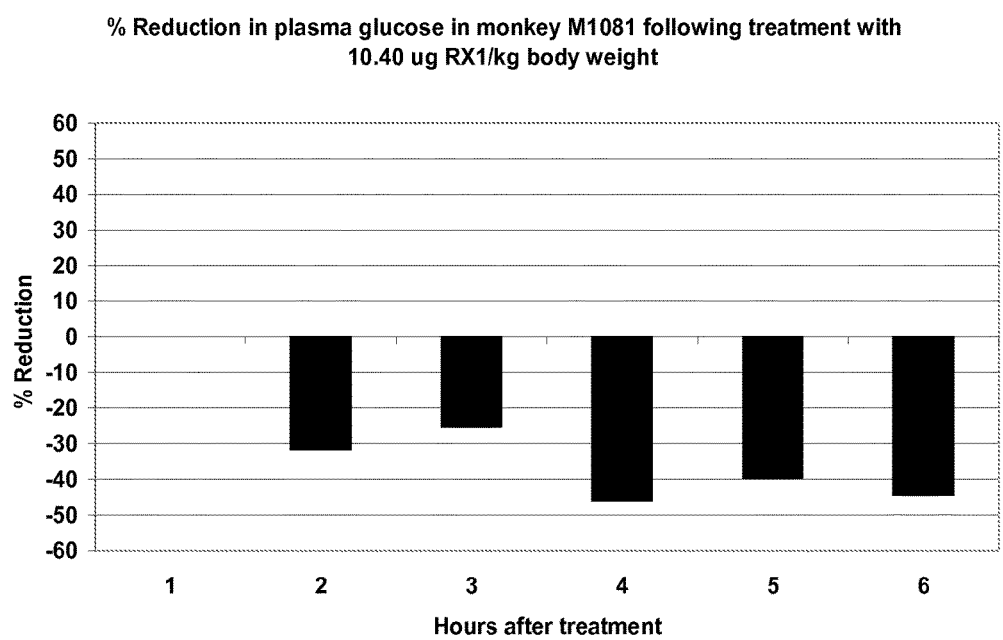
FIG. 1 is a graphical representation of percent reduction in glucose following RX1 treatment.

The term "dietary compositions" comprises any type of (fortified) food, (fortified) (animal) feed and beverages including also clinical nutrition, and also dietary supplements as well as the corresponding additives: food additives, beverage additives, feed additives. Also encompassed is functional food/feed i.e. a food/feed that has been enhanced with vitamins or pharmaceuticals to provide further specific health benefits, as well as a nutraceutical, i.e. a pill or other pharmaceutical product that has nutritional value.

The dietary compositions according to the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellyfying agents, gel forming agents, antioxidants and antimicrobials.

Another object of the present invention is a pharmaceutical composition containing at least one compound of the formula I-IV as defined and with the preferences given as above and a conventional pharmaceutical carrier.

Beside a pharmaceutically acceptable carrier and at least one compound of the formula I-IV the pharmaceutical compositions according to the present invention may further contain conventional pharmaceutical additives and adjuvants, excipients or diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like. The carrier material can be organic or inorganic inert carrier material suitable for oral/parenteral/injectable administration.

The dietary and pharmaceutical compositions according to the present invention may be in any galenic form that is suitable for administrating to the animal body including the human body, especially in any form that is conventional for oral administration, e.g. in solid form such as (additives/supplements for) food or feed, food or feed premix, fortified food or feed, tablets, pills, granules, dragees, capsules, and effervescent formulations such as powders and tablets, or in liquid form such as solutions, emulsions or suspensions as e.g. beverages, pastes and oily suspensions. The pastes may be filled into hard or soft shell capsules, whereby the capsules feature e.g. a matrix of (fish, swine, poultry, cow) gelatin, plant proteins or ligninsulfonate. Examples for other application forms are forms for sublingual, transdermal, parenteral or injectable administration. The dietary and pharmaceutical compositions may be in the form of controlled (delayed) release formulations. Furthermore, it has been demonstrated that by binding the compounds of the present invention to secondary molecules, such as certain peptides, increased is stability prolonging the active period is achieved. The present invention also encompasses prodrugs which are metabolised into more active entities.

Beverages encompass non-alcoholic and alcoholic drinks as well as liquid preparations to be added to drinking water and liquid food. Non-alcoholic drinks are e.g. soft drinks, sport drinks, fruit juices, lemonades, near-water drinks (i.e. water-based drinks with a low calorie content), teas and milk based drinks. Liquid food is e.g. soups and dairy products.

The compounds of the formula I-IV as well as (mixtures of) plant materials and plant extracts containing them, and dietary/pharmaceutical compositions containing them are thus suitable for the treatment of animals including humans.

Therefore, the invention relates to a method for the treatment of T1D and/or non-autoimmune T2D, obesity and/or syndrome X in animals including humans, said method comprising the step of administering an effective dose of a compound of the formula I as defined above to animals including humans which are in need thereof.

Animals in the context of the present invention may be mammals including humans. Preferred examples of mammals beside humans are other primates, dogs, cats, guinea pigs, rabbits, hares, ferrets, horses, and ruminants (cattle, sheep and goats). For humans a suitable daily dosage of a compound of the formula I-IV may be within the range from 0.00003 mg per kg body weight to 60 mg per kg body weight per day. More preferred may be a daily dosage of 0.0003 to 6 mg per kg body weight, preferred may be a daily dosage of 0.0003 to 3 mg per kg body weight per day, especially preferred may be a daily dosage of 0.003 to 0.3 mg per kg body weight per day, most preferred may be a daily dosage of 0.015 to 0.06 mg per kg body weight per day.

Compounds of the present invention may crystallize in more than one form, a characteristic known as polymorphism, and such polymorphic forms ("polymorphs") are within the scope of compounds of the invention. Polymorphism generally can occur as a response to changes in temperature, pressure, or both, and can also result from variations in the crystallization process. Polymorphs can be distinguished by various physical characteristics such as x-ray diffraction patterns, solubility, and melting point.

Certain of the compounds described herein may be capable of existing as stereoisomers such as by having a chiral carbon, sulfoxide sulfur or double bond whereby the compounds may exist as R or S enantiomers or E or Z isomers. The scope of the present invention includes all such individual isomers, racemates, purified enantiomers, and enantiomerically enriched mixtures of the compounds of the present invention.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

Included within the scope of the invention compounds are solvates of compounds of the depicted formula. "Solvate" refers to a complex of variable stoichiometry formed by a solute (in this invention, a compound of the present invention, or a salt or physiologically functional derivative thereof) and a solvent. Such solvents, for the purpose of the invention, should not interfere with the biological activity of the solute. Preferably the solvent used is a pharmaceutically acceptable solvent such as water, ethanol, and acetic acid.

The compounds according to the invention may be obtained using methods of synthesis known in principle. Preferably the compounds are obtained by the following methods according to the invention which are described in more detail hereinafter.

The following descriptions of preferred methods of synthesis relate to end products in a β-D-glucopyranosyl and β-D-galactopyranosyl configuration. The synthesis of the corresponding compounds in the α-D-glucopyranosyl or α-L-glucopyranosyl configuration (or any other pyranoses or furanoses) will be evident to the skilled man by analogy, and for this reason no further explanations and synthesis diagrams are provided, in the interests of clarity.

General synthetic routes to obtain the compounds of the compounds of the present invention are given in the following schemes.

General Synthetic Route 1 (RX-2 and RX-3)

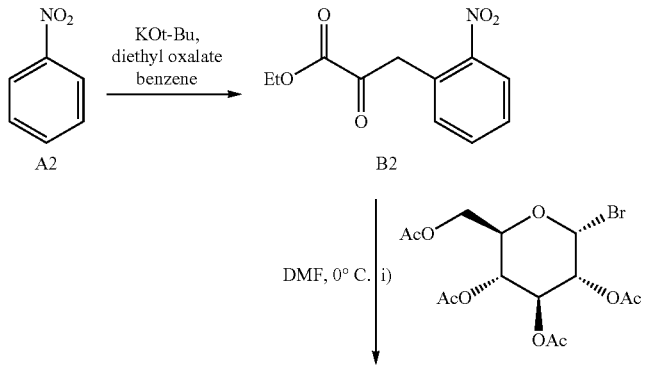

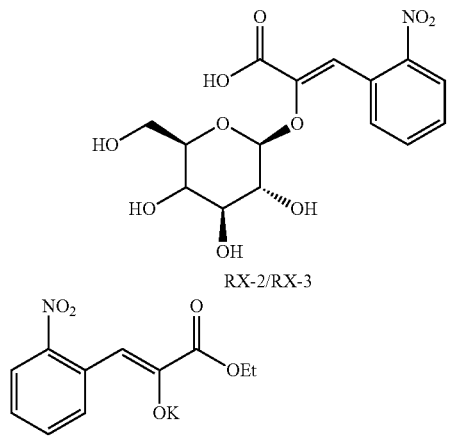

RX-2/RX-3

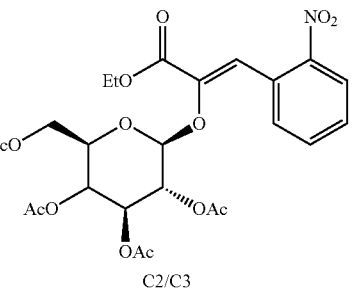

C2/C3

← LiOH / H₂O, THF

Potassium (Z)-3-ethoxy-1-(2-nitrophenyl)-3-oxo-prop-1-en-2-olate (B2)

The synthesis was performed according to Khour and Skibo (J. Org. Chem. 2007, 72, 8636-8647). To a slurry of potassium t-butoxide (1.64 g, 14.58 mmol) in 10 mL of dry benzene under nitrogen was added diethyl oxalate (2.1 g, 14.58 mmol). A solution of 2-nitrotoluene (2 g, 14.56 mmol) in 30 mL of dry benzene was added dropwise and a red solid formed immediately. The reaction mixture was further stirred at room temperature for 45 min. The red solid precipitate was collected by filtration and washed with benzene to afford the potassium salt of ethyl 3-(2-nitrophenyl)-2-oxopropanoate B2 in 68% yield.

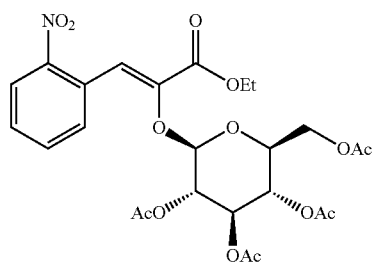 [SMILES: CCOC(=O)/C(=C/c1ccccc1[N+](=O)[O-])O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-3-ethoxy-1-(2-nitrophenyl)-3-oxoprop-1-en-2-yl)oxy)tetrahydro-2H-pyran-3,4,5-triyl triacetate (C2)

A solution of the potassium salt of 2-nitrophenylpyruvate B2 (100 mg, 0.36 mmol) in dry DMF (3 mL) was added dropwise over a period of 15 min, to a pre-cooled stirred solution of 2,3,4,6-tetra-O-acetyl-α-D-glucose (149 mg, 0.36 mmol) in dry DMF (2 mL) at 0° C. under nitrogen atmosphere. The temperature was gradually raised to room temperature. Reaction mixture was allowed to stir for 15 h, and the reaction was quenched with chilled, saturated aq. NaCl (25 mL). Extraction with ethyl acetate (3×30 mL), drying (MgSO₄), concentration under reduced pressure, and purification by flash chromatography (SiO₂, hexane-benzene-acetone-methanol, 5:4:5:1) to isolate the pure resultant compound C2 in 40% yield.

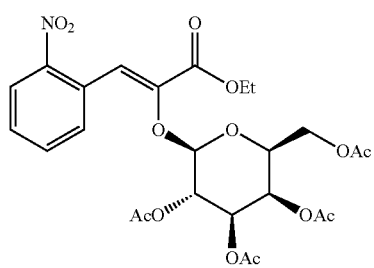 [SMILES: CCOC(=O)/C(=C/c1ccccc1[N+](=O)[O-])O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-ethoxy-1-(2-nitrophenyl)-3-oxoprop-1-en-2-yl)oxy)tetrahydro-2H-pyran-3,4,5-triyl triacetate (C3)

The solution of potassium salt of 2-nitrophenylpyruvate B2 (100 mg, 0.36 mmol) in dry DMF (3 mL) was added dropwise over a period of 15 min, to a pre-cooled stirred solution of 2,3,4,6-tetra-O-acetyl-α-D-galactose (149 mg, 0.36 mmol) in dry DMF (2 mL) at 0° C. under nitrogen atmosphere. The temperature was gradually raised to room temperature. Reaction mixture was allowed to stir for 15 h, and the reaction was quenched with chilled, saturated aq. NaCl (25 mL). Extraction with ethyl acetate (3×30 mL), drying (MgSO₄), concentration under reduced pressure, and purification by flash chromatography (SiO₂, hexane-benzene-acetone-methanol, 5:4:5:1) to isolate the pure resultant compound C3 in 50% yield.

Step 3: Hydrolysis

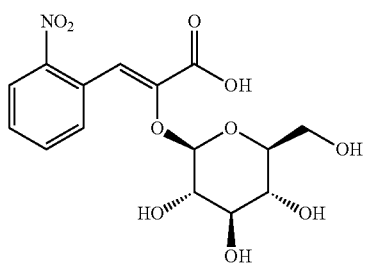 [SMILES: O=C(O)/C(=C/c1ccccc1[N+](=O)[O-])O[C@H]1O[C@@H](CO)[C@H](O)[C@@H](O)[C@@H]1O]

(Z)-3-(2-Nitrophenyl)-2-(((2R,3S,4R,5R,6S)-3,4,5-trihydroxy-6-(hydroxymethyl)tetrahydro-2H-pyran-2-yl)oxy)acrylic acid (RX-2)

The ester C2 (20 mg, 0.035 mmol) was dissolved in THF (0.4 mL) and added a solution of LiOH (8.44 mg, 0.352 mmol) in 0.3 mL water. The reaction mixture was stirred at room temperature for 3 hours. The solvent was evaporated and reaction mixture was acidified by using 0.1% TFA solution in water until pH<5. The solution was filtered and freeze-dried to give RX-2 as light yellow solid along with lithium trifluoroacetate salt, which was further purified by preparative HPLC using acetonitrile-water as an eluent and isolated the product as a white solid in quantitative yield after freeze drying: $^1$H NMR (400 MHz, MeOH-$d_4$): δ 8.22 (d, J=7.9 Hz, 1H), 7.90 (dd, J=8.2, 1.2 Hz, 1H), 7.70-7.56 (m, 1H), 7.52-7.38 (m, 1H), 7.03 (s, 1H), 5.04 (d, J=7.4 Hz, 1H), 3.74 (dd, J=12.0, 2.4 Hz, 1H), 3.63 (dd, J=12.0, 5.2 Hz, 1H), 3.44-3.34 (m, 3H), 3.21 (m, 1H); ESI-HRMS m/z: calcd for $C_{15}H_{17}NO_{10}Na^+$: 394.0745. found 394.0755.

(Z)-3-(2-Nitrophenyl)-2-(((2R,3S,4R,5S,6S)-3,4,5-trihydroxy-6-(hydroxymethyl)tetrahydro-2H-pyran-2-yl)oxy)acrylic acid (RX-3)

The ester C3 (20 mg, 0.035 mmol) was dissolved in THF (0.4 mL) and added a solution of LiOH (8.44 mg, 0.352 mmol) in 0.3 mL water. The reaction mixture was stirred at room temperature for 3 hours. The solvent was evaporated and reaction mixture was acidified by using 0.1% TFA solution in water until pH<5. The solution was filtered and freeze-dried to give the compound RX-3 as light yellow solid along with lithium trifluoroacetate salt, which was further purified by preparative HPLC using acetonitrile-water as an eluent and isolated as a white solid in quantitative yield after freeze drying: $^1$H NMR (400 MHz, MeOH-$d_4$): δ 8.12 (d, J=7.8 Hz, 1H), 7.86 (d, J=8.1 Hz, 1H), 7.55 (t, J=7.6 Hz, 1H), 7.39 (t, J=7.8 Hz, 1H), 7.19 (s, 1H), 4.96 (d, J=7.7 Hz, 1H), 3.73 (d, J=3.0 Hz, 1H), 3.65-3.44 (m, 3H), 3.39 (dd, J=9.7, 3.3 Hz, 1H), 3.34 (t, J=6.1 Hz, 1H); $^{13}$C NMR (101 MHz, MeOH-$d_4$): δ 149.85, 146.87, 133.87, 133.83, 129.83, 129.76, 125.01, 119.00, 103.57, 77.10, 74.96, 72.76, 69.93, 61.90; ESI-HRMS m/z: calcd for $C_{15}H_{17}NO_{10}Na^+$: 394.0745. found 394.075.

Synthesis of RX-4 to RX-30
(Intermediate B18 was Synthesized by an Alternative Route)

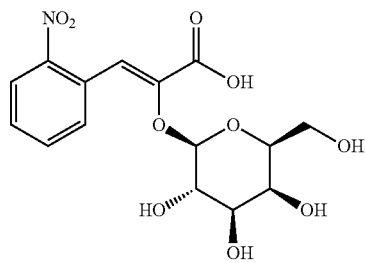 [SMILES: O=C(O)/C(=C/c1ccccc1[N+](=O)[O-])O[C@H]1O[C@@H](CO)[C@@H](O)[C@@H](O)[C@@H]1O]

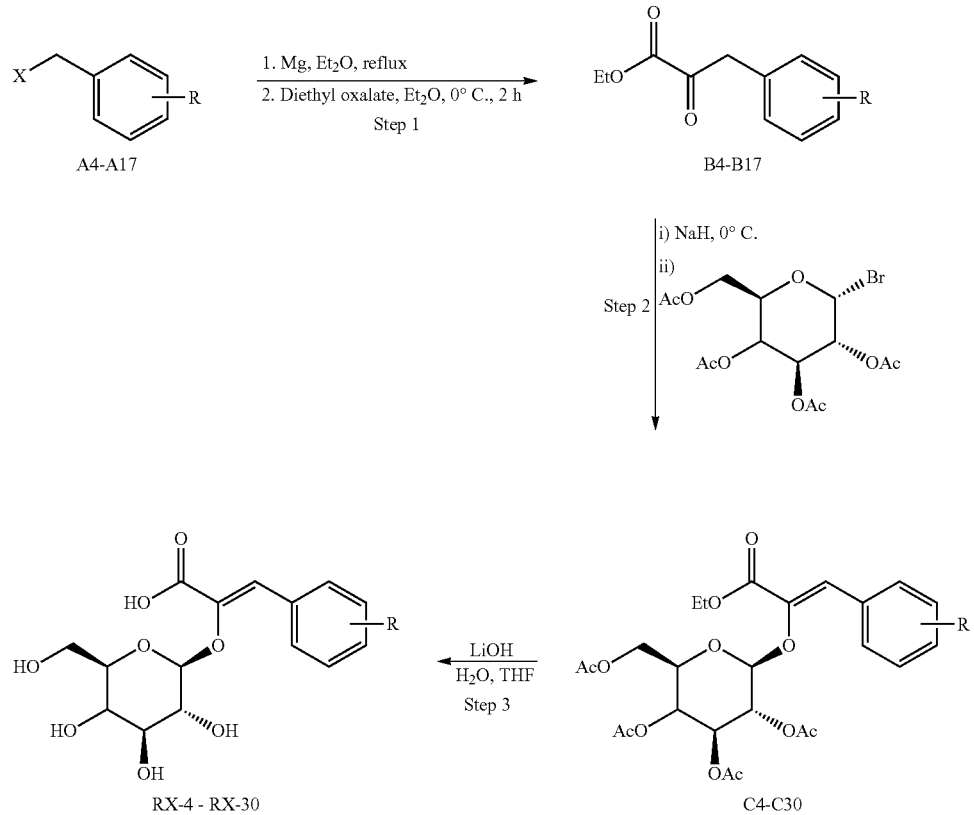

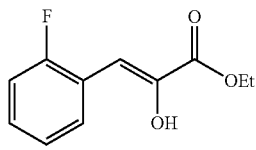

Ethyl (2-fluorophenyl)pyruvate (B4)

To a suspension of Mg turnings (0.231 g, 9.51 mmol) in diethyl ether (1.5 mL) was added a solution of 2-fluorobenzyl chloride (1.25 g, 8.65 mmol) in diethyl ether (9 mL) dropwise to the refluxing reaction mixture. The mixture was stirred for 10 min, cooled to room temperature and added dropwise to a solution of diethyl oxalate (2.53 g, 17.29 mmol) in diethyl ether (17 mL) at 0° C. The reaction mixture was stirred at room temperature for 2 hours, quenched with 1M aqueous hydrochloric acid and extracted with diethyl ether. The combined extracts were washed with brine, dried over magnesium sulfate, and concentrated under reduced pressure. The excess of diethyl oxalate was removed by bulb to bulb distillation at room temperature and the residue was purified by flash chromatography (SiO$_2$, 15-20% ethyl acetate in petroleum ether) to give the resulting compound B4 as colorless oil in 70% yield which was used instantly in next step.

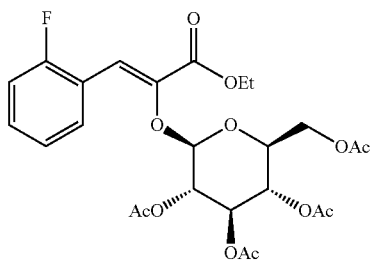

(2S,3S,4R,5S,6R)-2-(Acetoxymethyl)-6-(((Z)-3-ethoxy-1-(2-fluorophenyl)-3-oxoprop-1-en-2-yl)oxy)tetrahydro-2H-pyran-3,4,5-triyl triacetate (C4)

The reactions were preformed according to Marais et al. (J. Chem. Soc., Perkin Trans. 1, 1996, 2915-2918): The ethyl 3-(2-fluorophenyl)-2-oxopropanoate B4 (100 mg, 0.476 mmol) in dry DMF (3.3 mL) was transferred dropwise under anhydrous conditions and nitrogen atmosphere (over a period of 15 min) to a vigorously stirred suspension of sodium hydride (13 mg, 0.523 mmol) in DMF (3.0 mL) at 0° C. This mixture was stirred for a further 1 h at 0° C. and was added dropwise to a vigorously stirred solution of 2,3,4,6-tetra-O-acetyl-α-D-glucose bromide (196 mg, 0.476 mmol) in dry DMF (3 mL) at 0° C. The temperature was raised to room temperature, stirring was continued for 15 h, and the reaction was quenched with chilled, saturated aq. NaCl (10 mL). Extraction with ethyl acetate (3×25 mL), drying (MgSO$_4$), concentration under reduced pressure, and purification by flash chromatography (SiO$_2$, hexane-benzene-acetone-methanol, 5:4:5:1) to isolate the resulting compound along with glycal impurity which was further purified by preparative HPLC to isolate the pure resultant compound C4 in the form of white solid in 22% yield.

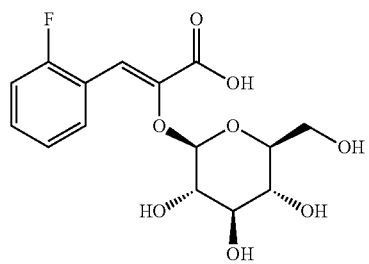 [SMILES: O=C(O)/C(=C/c1ccccc1F)O[C@H]1O[C@@H](CO)[C@H](O)[C@@H](O)[C@@H]1O]

(Z)-3-(2-Fluorophenyl)-2-(((2R,3S,4R,5R,6S)-3,4,5-trihydroxy-6-(hydroxymethyl)tetrahydro-2H-pyran-2-yl)oxy)acrylic acid (RX-4)

The ester C4 (20 mg, 0.037 mmol) was dissolved in THF (0.4 mL) and added a solution of LiOH.H$_2$O (8.86 mg, 0.37 mmol) in water (0.3 mL). The reaction mixture was stirred at room temperature for one hour and then acidified until pH<3 with Dowex 50-X8 resin, filtered and concentrated, and the residue was purified by preparative HPLC using acetonitrile-water as an eluent. After freeze drying, the final product was isolated in 87% yield: $^1$H NMR (400 MHz, MeOH-d$_4$): δ 8.31 (t, J=7.1 Hz, 1H), 7.24 (dd, J=13.6, 5.8 Hz, 1H), 7.14 (s, 1H), 7.07 (t, J=7.6 Hz, 1H), 7.03-6.96 (m, 1H), 5.17 (d, J=7.4 Hz, 1H), 3.66 (dd, J=12.0, 2.2 Hz, 1H), 3.52 (dd, J=12.0, 5.2 Hz, 1H), 3.41-3.23 (m, 3H), 3.17-3.11 (m, 1H); $^{13}$C NMR (101 MHz, MeOH-d$_4$): δ 166.72, 161.83 (d, $^1J_{C,F}$=249.7 Hz), 144.28, 132.66, 131.71, 125.15, 122.48, 115.93 (d, 1C), 115.78 (d, 1C), 102.66, 78.59, 78.07, 75.64, 71.35, 62.50; ESI-HRMS m/z: calcd for C$_{15}$H$_{17}$FO$_8$Na$^+$: 367.0800. found 367.0800.

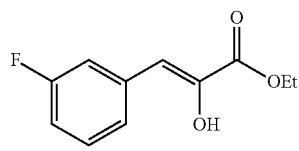 [SMILES: CCOC(=O)/C(O)=C/c1cccc(F)c1]

Ethyl (3-fluorophenyl)pyruvate (B5)

The title compound was prepared as described for B4 using 3-fluorobenzyl bromide (1.250 g, 8.64 mmol), magnesium (0.231 g, 9.51 mmol) and diethyl oxalate (2.52 g, 17.30 mmol) in the form of colorless oil in 80% yield and used instantly in next step.

C5

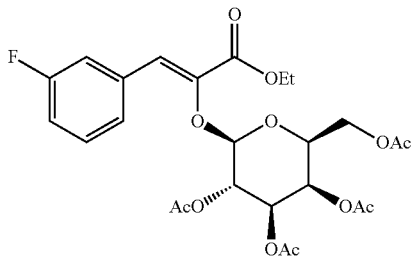 [SMILES: CCOC(=O)/C(=C/c1cccc(F)c1)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-ethoxy-1-(3-fluorophenyl)-3-oxoprop-1-en-2-yl)oxy)tetrahydro-2H-pyran-3,4,5-triyl triacetate (C5)

The title compound was prepared as described for C4 by using ethyl 3-(3-fluorophenyl)-2-oxopropanoate B5 (100 mg, 0.476 mmol), sodium hydride (13 mg, 0.523 mmol) and 2,3,4,6-tetra-O-acetyl-α-D-galactose bromide (196 mg, 0.476 mmol). The compound was isolated in the form of white solid in 79% yield.

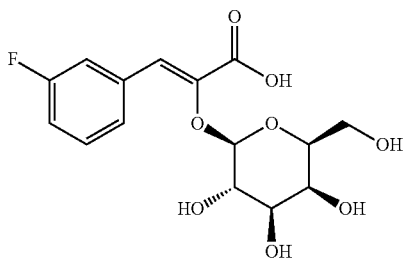 [SMILES: O=C(O)/C(=C/c1cccc(F)c1)O[C@H]1O[C@@H](CO)[C@@H](O)[C@@H](O)[C@@H]1O]

(Z)-3-(3-Fluorophenyl)-2-(((2R,3S,4R,5S,6S)-3,4,5-trihydroxy-6-(hydroxymethyl)tetrahydro-2H-pyran-2-yl)oxy)acrylic acid (RX-5)

The title compounds was prepared as described for RX-4 to give the product as a white solid in 85% yield: $^1$H NMR (400 MHz, MeOH-d$_4$): δ 7.66 (d, J=10.9 Hz, 1H), 7.47 (d, J=7.8 Hz, 1H), 7.23 (m, 1H), 6.92 (m, 1H), 6.87 (s, 1H), 5.05 (d, J=7.8 Hz, 1H), 3.79-3.68 (m, 2H), 3.56 (m, 2H), 3.47-3.36 (m, 2H); $^{13}$C NMR (101 MHz, MeOH-d$_4$): δ 167.75, 164.06 (d, $^1J_{C,F}$=243.1 Hz), 137.21 (d, $^3J_{C,F}$=8.6 Hz), 130.79 (d, $^3J_{C,F}$=8.3 Hz), 127.62, 127.59, 123.12, 117.71 (d, $^2J_{C,F}$=23.0 Hz), 116.29 (d, $^2J_{C,F}$=21.6 Hz), 103.66, 77.27, 75.15, 72.99, 70.03, 61.99; ESI-HRMS m/z: calcd for C$_{15}$H$_{17}$FO$_8$Na$^+$: 367.0800. found 367.0796.

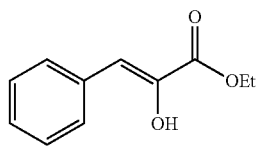 [SMILES: CCOC(=O)/C(O)=C/c1ccccc1]

Ethyl phenylpyruvate (B6)

The title compound was prepared as described for B4 using benzyl bromide (1.250 g, 7.31 mmol), magnesium (0.195 g, 8.04 mmol) and diethyl oxalate (2.136 g, 14.62 mmol) in the form of colorless oil in 80% yield and used instantly in next step.

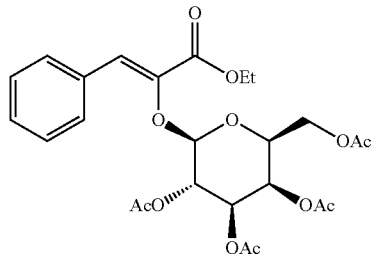 [SMILES: CCOC(=O)/C(=C/c1ccccc1)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-ethoxy-3-oxo-1-phenylprop-1-en-2-yl)oxy)tetrahydro-2H-pyran-3,4,5-triyl triacetate (C6)

The title compound was prepared as described for C4 using (ethyl 3-(phenyl)-2-oxopropanoate B6 (100 mg, 0.520 mmol), sodium hydride (13.73 mg, 0.572 mmol) and 2,3,4,6-tetra-O-acetyl-α-D-galactose bromide (214 mg, 0.520 mmol). The resulting compound was isolated in the form of white solid in 37% yield.

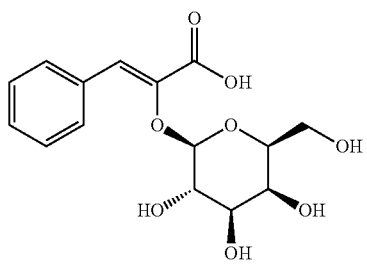 [SMILES: O=C(O)/C(=C/c1ccccc1)O[C@H]1O[C@@H](CO)[C@@H](O)[C@@H](O)[C@@H]1O]

(Z)-3-Phenyl-2-(((2R,3S,4R,5S,6S)-3,4,5-trihydroxy-6-(hydroxymethyl)tetrahydro-2H-pyran-2-yl)oxy)acrylic acid (RX-6)

The title compound was prepared as described for RX-4 to give the product as a white solid in 92% yield: $^1$H NMR (400 MHz, MeOH-d$_4$) δ 7.86 (d, J=7.3 Hz, 2H), 7.30 (t, J=7.4 Hz, 2H), 7.23 (m, 1H), 6.81 (s, 1H), 4.97 (d, J=7.6 Hz, 1H), 3.90-3.81 (m, 2H), 3.72-3.62 (m, 2H), 3.58-3.48 (m, 2H); ESI-HRMS m/z: calcd for C$_{15}$H$_{18}$ClO$_8$Na$^+$: 348.0821. found 348.0812.

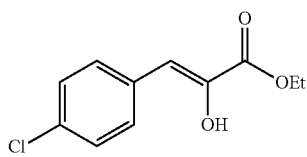 [SMILES: CCOC(=O)/C(O)=C/c1ccc(Cl)cc1]

Ethyl (4-chlorophenyl)pyruvate (B7)

The title compound was prepared as described for B4 using 4-chlorobenzyl chloride (1.250 g, 7.76 mmol), magnesium (0.208 g, 8.54 mmol) and diethyl oxalate (2.269 g, 15.53 mmol). The product was isolated in the form of colorless oil in 74% yield and used instantly in next step.

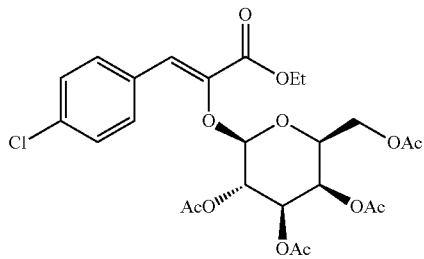 [SMILES: CCOC(=O)/C(=C/c1ccc(Cl)cc1)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-1-(4-chlorophenyl)-3-ethoxy-3-oxoprop-1-en-2-yl)oxy)tetrahydro-2H-pyran-3,4,5-triyl triacetate (C7)

This was prepared as described for C4 using ethyl 3-(4-chlorophenyl)-2-oxopropanoate B7 (100 mg, 0.441 mmol), sodium hydride (11.65 mg, 0.485 mmol) and 2,3,4,6-tetra-O-acetyl-α-D-galactose bromide (181 mg, 0.441 mmol). The resulting compound was isolated in the form of white solid in 66% yield.

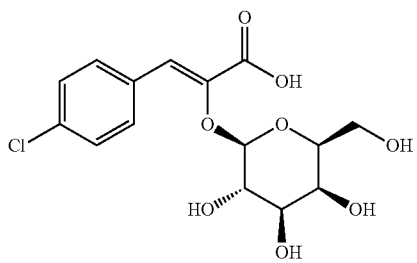 [SMILES: O=C(O)/C(=C/c1ccc(Cl)cc1)O[C@H]1O[C@@H](CO)[C@@H](O)[C@@H](O)[C@@H]1O]

(Z)-3-(4-Chlorophenyl)-2-(((2R,3S,4R,5S,6S)-3,4,5-trihydroxy-6-(hydroxymethyl)tetrahydro-2H-pyran-2-yl)oxy)acrylic acid (RX-7)

This was prepared as described for (RX-4) in the form of white solid in 93% yield: $^1$H NMR (400 MHz, MeOH-d$_4$): δ 7.74 (d, J=8.6 Hz, 2H), 7.17 (d, J=8.6 Hz, 2H), 6.64 (s, 1H), 4.88 (d, J=7.8 Hz, 1H), 3.78-3.66 (m, 2H), 3.57 (m, 2H), 3.41 (m, 2H); $^{13}$C NMR (101 MHz, MeOH-d$_4$): δ 171.46, 150.37, 134.73, 134.15, 132.59 (2C), 129.13 (2C), 118.94, 104.39, 77.36, 75.63, 73.17, 70.13, 62.15; ESI-HRMS m/z: calcd for $C_{15}H_{17}ClO_8Na^+$: 383.0505. found 383.0515.

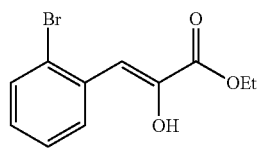 [SMILES: CCOC(=O)/C(O)=C/c1ccccc1Br]

Ethyl (2-bromophenyl)pyruvate (B8)

The title compound was prepared as described for (B4) using 2-bromobenzyl bromide (1.250 g, 5.00 mmol), magnesium (0.134 g, 5.50 mmol) and diethyl oxalate (1.462 g, 10.00 mmol). The product was isolated in the form of colorless oil in 80% yield and used instantly in next step.

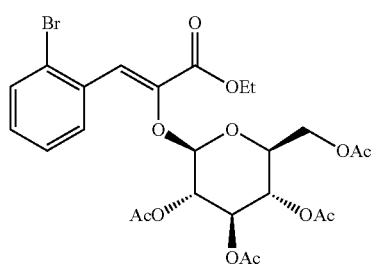 [SMILES: CCOC(=O)/C(=C/c1ccccc1Br)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-1-(2-bromophenyl)-3-ethoxy-3-oxoprop-1-en-2-yl)oxy)tetrahydro-2H-pyran-3,4,5-triyl triacetate (C8)

The title compound was prepared as described for C4 using ethyl 3-(2-bromophenyl)-2-oxopropanoate B8 (100 mg, 0.369 mmol), sodium hydride (9.74 mg, 0.406 mmol) and 2,3,4,6 tetra-O-acetyl-α-D-glucose bromide (152 mg, 0.369 mmol). The resulting compound was isolated in the form of white solid in 17% yield.

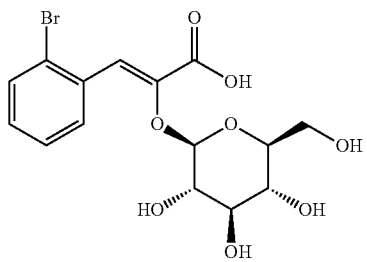 [SMILES: O=C(O)/C(=C/c1ccccc1Br)O[C@H]1O[C@@H](CO)[C@H](O)[C@@H](O)[C@@H]1O]

(Z)-3-(2-Bromophenyl)-2-(((2R,3S,4R,5R,6S)-3,4,5-trihydroxy-6-(hydroxymethyl)tetrahydro-2H-pyran-2-yl)oxy)acrylic acid (RX-8)

The title compound was prepared as described for RX-4 to give the product as a white solid in 88% yield: $^1$H NMR (400 MHz, MeOH-d$_4$): δ 8.21 (d, J=7.8 Hz, 1H), 7.51 (d, J=8.0 Hz, 1H), 7.33-7.21 (m, 2H), 7.10 (t, J=8.4 Hz, 1H), 5.13 (d, J=7.4 Hz, 1H), 3.67 (dd, J=12.0, 2.2 Hz, 1H), 3.54 (dd, J=12.0, 5.1 Hz, 1H), 3.32-3.23 (m, 3H), 3.12 (m, 1H); $^{13}$C NMR (101 MHz, MeOH-d$_4$): δ 166.77, 144.20, 134.41, 133.66, 133.26, 131.14, 128.38, 125.54, 123.23, 102.58, 78.52, 77.99, 75.51, 71.29, 62.45; ESI-HRMS m/z: calcd for $C_{15}H_{17}BrO_8Na^+$: 427.0000. found 427.0002.

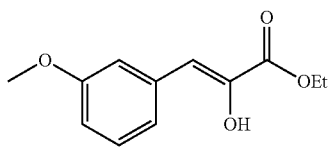 [SMILES: CCOC(=O)/C(O)=C/c1cccc(OC)c1]

Ethyl (3-methoxyphenyl)pyruvate (B9)

The title compound was prepared as described for B4 using 3-methoxybenzyl bromide (1.5 g, 7.46 mmol), magnesium (0.199 g, 8.21 mmol) and diethyl oxalate (2.18 g, 14.92 mmol). The product was isolated in the form of colorless oil in 74% yield and used instantly in next step.

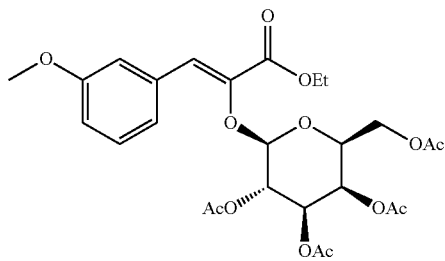 [SMILES: CCOC(=O)/C(=C/c1cccc(OC)c1)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-ethoxy-1-(3-methoxyphenyl)-3-oxoprop-1-en-2-yl)oxy)tetrahydro-2H-pyran-3,4,5-triyl triacetate (C9)

The title compound was prepared as described for C4 using ethyl 3-(3-methoxyphenyl)-2-oxopropanoate B9 (100 mg, 0.369 mmol), sodium hydride (11.88 mg, 0.495 mmol) and 2,3,4,6 tetra-O-acetyl-α-D-galactose bromide (185 mg, 0.450 mmol). The resulting compound was isolated in the form of white solid in 62% yield.

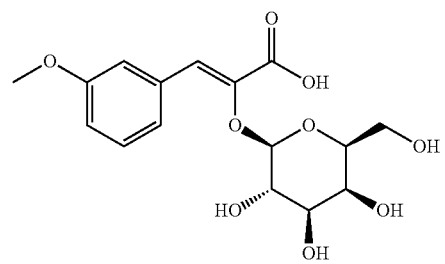 [SMILES: COc1cccc(/C=C(\O[C@H]2O[C@@H](CO)[C@@H](O)[C@@H](O)[C@@H]2O)C(=O)O)c1]

(Z)-3-(3-M ethoxyphenyl)-2-(((2R,3S,4R,5S,6S)-3,4,5-trihydroxy-6(hydroxymethyl)tetrahydro-2H-pyran-2-yl)oxy)acrylic acid (RX-9)

The title compound was prepared as described for RX-4 to give the product as a white solid in 94% yield: $^1$H NMR (400 MHz, MeOH-d$_4$): δ 7.73 (s, 1H), 7.30-7.17 (m, 2H), 7.05 (s, 1H), 6.86 (dd, J=7.1, 2.3 Hz, 1H), 5.14 (d, J=7.7 Hz, 1H), 3.89-3.80 (m, 5H), 3.66 (ddd, J=25.2, 11.2, 6.2 Hz, 2H), 3.54 (dd, J=9.6, 3.4 Hz, 1H), 3.48 (t, J=6.0 Hz, 1H); $^{13}$C NMR (101 MHz, MeOH-d$_4$): δ 167.38, 160.97, 142.92, 135.86, 130.10, 126.16, 124.56, 117.14, 115.56, 103.57, 77.19, 75.01, 73.09, 70.00, 62.08, 55.98; ESI-HRMS m/z: calcd for $C_{16}H_{20}O_9Na^+$: 379.1107. found 379.1010.

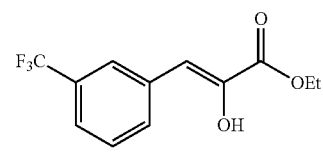 [SMILES: CCOC(=O)/C(O)=C/c1cccc(C(F)(F)F)c1]

Ethyl (3-trifluoromethylphenyl)pyruvate (B10)

The title compound was prepared as described for B4 using 3-trifluoromethylbenzyl bromide (2.5 g, 10.46 mmol), magnesium (0.280 g, 11.50 mmol) and diethyl oxalate (3.06 g, 20.92 mmol). The product was isolated in the form of colorless oil in 78% yield and use instantly in next step.

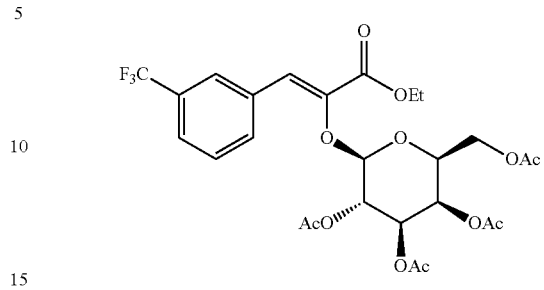

(2S,3R,4R,5S,6R)-2-(Acetoxymethyl)-6-(((Z)-3-ethoxy-3-oxo-1-(3 (trifluoromethyl)phenyl)prop-1-en-2-yl)oxy)tetrahydro-2H-pyran-3,4,5-triyl triacetate (C10)

The title compound was prepared as described for C4 using ethyl 3-(3-(trifluoromethyl)phenyl)-2-oxopropanoate B10 (100 mg, 0.384 mmol), sodium hydride (10.14 mg, 0.544 mmol) and 2,3,4,6 tetra-O-acetyl-α-D-galactose bromide (158 mg, 0.384 mmol). The resulting compound was isolated in the form of white solid in 22% yield.

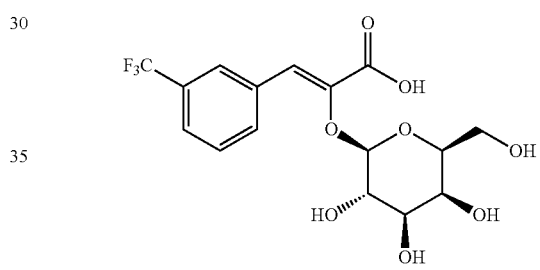

(Z)-3-(3-(Trifluoromethyl)phenyl)-2-(((2R,3S,4R,5S,6S)-3,4,5-trihydroxy-6-(hydroxymethyl)tetrahydro-2H-pyran-2-yl)oxy)acrylic acid (RX-10)

The title compound was prepared as described for RX-4 to give the product as a white solid in 96% yield: $^1$H NMR (400 MHz, MeOH-d$_4$): δ 8.16-7.99 (m, 2H), 7.46 (m, 2H), 7.00 (s, 1H), 5.10 (d, J=7.7 Hz, 1H), 3.79-3.69 (m, 2H), 3.55 (m, 2H), 3.47-3.37 (m, 2H); $^{13}$C NMR (101 MHz, MeOH-d$_4$): δ 166.82, 144.41, 135.74, 135.03, 131.85, 131.53, 130.09, 128.11, 126.14, 123.80, 103.55, 77.20, 75.01, 72.94, 69.97, 61.97; ESI-HRMS m/z: calcd for $C_{16}H_{17}F_3O_8Na^+$: 417.0768. found 417.0767.

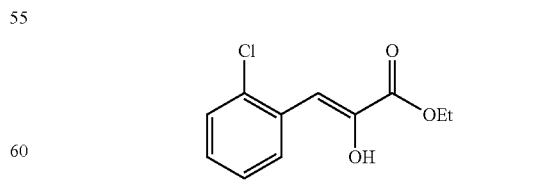

Ethyl (2-chlorophenyl)pyruvate (B11)

The title compound was prepared as described for B4 using 2-chlorobenzyl chloride (1.250 g, 7.76 mmol), magnesium (0.208 g, 8.54 mmol), diethyl oxalate (2.269 g, 15.53 mmol). The product was isolated in the form of colorless oil in 74% yield and use instantly in next step.

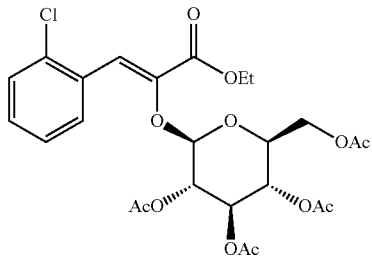 [SMILES: CCOC(=O)/C(=C/c1ccccc1Cl)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-1-(2-chlorophenyl)-3-ethoxy-3-oxoprop-1-en-2-yl)oxy) tetrahydro-2H-pyran-3,4,5-triyl triacetate (C11)

The title compound was prepared as described for C4 using ethyl 3-(2-chlorophenyl)-2-oxopropanoate B11 (100 mg, 0.441 mmol), sodium hydride (11.65 mg, 0.485 mmol) and 2,3,4,6 tetra-O-acetyl-α-D-glucose bromide (181 mg, 0.441 mmol). The resulting compound was isolated in the form of white solid in 16% yield.

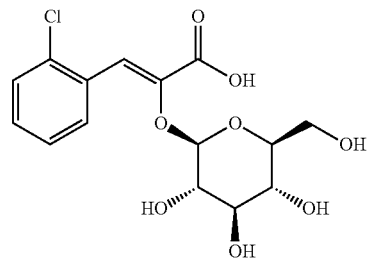 [SMILES: O=C(O)/C(=C/c1ccccc1Cl)O[C@H]1O[C@@H](CO)[C@H](O)[C@@H](O)[C@@H]1O]

(Z)-3-(2-Chlorophenyl)-2-(((2R,3S,4R,5R,6S)-3,4,5-tri hydroxy-6-(hydroxymethyl)tetrahydro-2H-pyran-2-yl)oxy)acrylic acid (RX-11)

The title compound was prepared as described for RX-4 to give the product as a white solid in 88% yield: $^1$H NMR (400 MHz, MeOH-$d_4$): δ 8.26 (d, J=9.1 Hz, 1H), 7.31 (m, 2H), 7.26-7.12 (m, 2H), 5.15 (d, J=7.0 Hz, 1H), 3.67 (d, J=12.0 Hz, 1H), 3.54 (dd, J=12.0, 5.1 Hz, 1H), 3.35-3.23 (m, 3H), 3.13 (m, 1H); $^{13}$C NMR (101 MHz, MeOH-$d_4$): δ 166.76, 144.33, 135.08, 133.11, 132.60, 130.99, 130.31, 127.83, 120.38, 102.58, 78.54, 78.00, 75.54, 71.29, 62.45; ESI-HRMS m/z: calcd for $C_{15}H_{17}ClO_8Na^+$: 383.0505. found 383.0490.

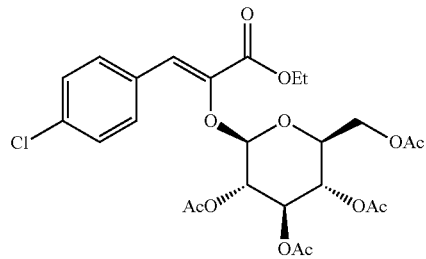 [SMILES: CCOC(=O)/C(=C/c1ccc(Cl)cc1)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-1-(4-chlorophenyl)-3-ethoxy-3-oxoprop-1-en-2-yl)oxy) tetrahydro-2H-pyran-3,4,5-triyl triacetate (C12)

The title compound was prepared as described for C4 using ethyl 3-(4-chlorophenyl)-2-oxopropanoate B7 (100 mg, 0.441 mmol), sodium hydride (11.65 mg, 0.485 mmol) and 2,3,4,6 tetra-O-acetyl-α-D-glucose bromide (181 mg, 0.441 mmol). The resulting compound was isolated in the form of white solid in 22% yield.

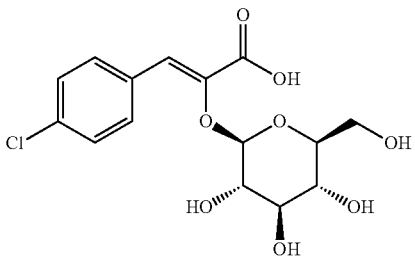 [SMILES: O=C(O)/C(=C/c1ccc(Cl)cc1)O[C@H]1O[C@@H](CO)[C@H](O)[C@@H](O)[C@@H]1O]

(Z)-3-(4-Chlorophenyl)-2-(((2R,3S,4R,5R,6S)-3,4,5-tri hydroxy-6-(hydroxymethyl)tetrahydro-2H-pyran-2-yl)oxy)acrylic acid (RX-12)

The title compound was prepared as described for RX-4 to give the product as a white solid in 84% yield: $^1$H NMR (400 MHz, MeOH-$d_4$) δ 7.76 (d, J=8.6 Hz, 2H), 7.25 (d, J=8.6 Hz, 2H), 6.92 (s, 1H), 5.12 (d, J=7.5 Hz, 1H), 3.66 (dd, J=12.0, 2.2 Hz, 1H), 3.52 (dd, J=12.0, 5.2 Hz, 1H), 3.33 (ddd, J=28.5, 18.0, 8.6 Hz, 3H), 3.17-3.10 (m, 1H); $^{13}$C NMR (101 MHz, MeOH-$d_4$): δ 166.98, 143.40, 135.62, 133.48, 133.10 (2C), 129.47 (2C), 124.26, 102.87, 78.58, 78.09, 75.65, 71.32, 62.50; ESI-HRMS m/z: calcd for $C_{15}H_{17}ClO_8Na^+$: 383.0505. found 383.0506.

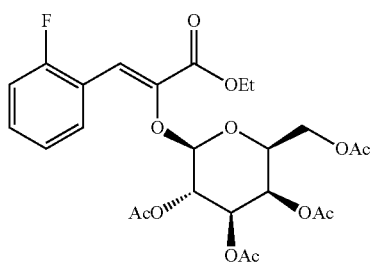 [SMILES: CCOC(=O)/C(=C/c1ccccc1F)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-ethoxy-1-(2-fluorophenyl)-3-oxoprop-1-en-2-yl)oxy) tetrahydro-2H-pyran-3,4,5-triyl triacetate (C13)

The title compound was prepared as described for (C4) by using ethyl 3-(2-fluorophenyl)-2-oxopropanoate B4 (100 mg, 0.476 mmol), sodium hydride (13 mg, 0.523 mmol) and 2,3,4,6-tetra-O-acetyl-α-D-galactose bromide (196 mg, 0.476 mmol). The compound was isolated in the form of white solid in 79% yield.

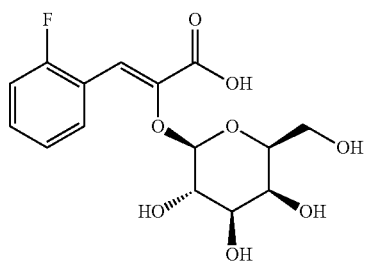

(Z)-3-(2-Fluorophenyl)-2-((2R,3S,4R,5S,6S)-3,4,5-trihydroxy-6-(hydroxymethyl)tetrahydro-2H-pyran-2-yl)oxy)acrylic acid (RX-13)

The title compound was prepared as described for RX-4 to give the product as a white solid in 96% yield: $^1$H NMR (400 MHz, MeOH-d$_4$): δ 8.36 (td, J=7.8, 1.6 Hz, 1H), 7.23 (ddd, J=15.4, 5.4, 1.7 Hz, 1H), 7.14 (s, 1H), 7.07 (t, J=7.7 Hz, 1H), 6.98 (ddd, J=10.7, 8.3, 1.1 Hz, 1H), 5.09 (d, J=7.7 Hz, 1H), 3.76 (dd, J=3.4, 0.8 Hz, 1H), 3.70 (dd, J=9.7, 7.7 Hz, 1H), 3.55 (ddd, J=26.3, 11.2, 6.2 Hz, 2H), 3.43 (dd, J=9.7, 3.4 Hz, 1H), 3.39 (td, J=6.2, 1.0 Hz, 1H); $^{13}$C NMR (101 MHz, MeOH-d$_4$): δ 169.41, 164.35 (d, $^1J_{C,F}$=249.6 Hz), 146.85, 135.46, 134.20, 127.77, 124.99, 118.45 (d, 1C), 118.37 (d, 1C), 105.94, 79.73, 77.48, 75.47, 72.53, 64.48; ESI-HRMS m/z: calcd for C$_{15}$H$_{17}$FO$_8$Na$^+$: 367.0800. found 367.0809.

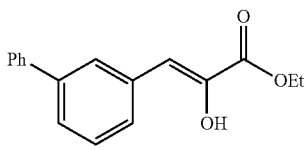 [SMILES: CCOC(=O)/C(O)=C/c1cccc(-c2ccccc2)c1]

Ethyl (3-phenylphenyl)pyruvate (B12)

The title compound was prepared as described for B4 using 3-phenylbenzyl bromide (1.250 g, 5.06 mmol), magnesium (0.135 g, 5.56 mmol) and diethyl oxalate (1.478 g, 10.12 mmol). The resulting compound was isolated in the form of colorless oil in 80% yield and use instantly in next step.

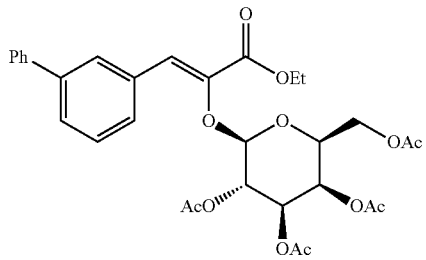 [SMILES: CCOC(=O)/C(=C/c1cccc(-c2ccccc2)c1)O[C@H]1O[C@@H](COC(C)=O)[C@@H](OC(C)=O)[C@@H](OC(C)=O)[C@@H]1OC(C)=O]

(2R,3S,4R,5R,6S)-2-(((Z)-1-([1,1'-Biphenyl]-3-yl)-3-ethoxy-3-oxoprop-1-en-2-yl)oxy)-6-(acetoxymethyl)tetrahydro-2H-pyran-3,4,5-triyl triacetate (C14)

The title compound was prepared as described for C4 using methyl 3-(3-arylphenyl)-2-oxopropanoate B12 (100 mg, 0.373 mmol), sodium hydride (9.0 mg, 0.373 mmol) and 2,3,4,6-tetra-O-acetyl-α-D-galactose bromide (153 mg, 0.373 mmol). The compound was isolated in the form of white solid in 26% yield.

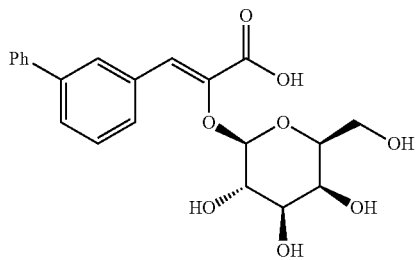 [SMILES: O=C(O)/C(=C/c1cccc(-c2ccccc2)c1)O[C@H]1O[C@@H](CO)[C@@H](O)[C@@H](O)[C@@H]1O]

(Z)-3-([1,1'-Biphenyl]-3-yl)-2-(((2R,3S,4R,5S,6S)-3,4,5-tri hydroxy-6-(hydroxymethyl)tetrahydro-2H-pyran-2-yl)oxy)acrylic acid (RX-14)

The title compound was prepared as described for RX-4 to give the product as a white solid in 98% yield: $^1$H NMR (400 MHz, MeOH-d$_4$): δ 8.24 (t, J=1.7 Hz, 1H), 7.70-7.58 (m, 3H), 7.53-7.47 (m, 1H), 7.38-7.29 (m, 3H), 7.26-7.19 (m, 1H), 7.06 (s, 1H), 5.05 (d, J=7.8 Hz, 1H), 3.78 (m, 2H), 3.56 (ddd, J=32.3, 11.2, 6.1 Hz, 2H), 3.46 (dd, J=9.7, 3.4 Hz, 1H), 3.41 (td, J=6.1, 0.9 Hz, 1H); $^{13}$C NMR (101 MHz, MeOH-d$_4$): δ 167.41, 143.18, 142.36, 141.97, 135.12, 130.78, 130.17, 129.94 (2C), 129.81, 128.52, 128.41, 128.17 (2C), 126.29, 103.89, 77.23, 75.06, 73.08, 69.99, 62.09; ESI-HRMS m/z: calcd for C$_{21}$H$_{22}$O$_8$Na$^+$: 425.1207. found 425.1216.

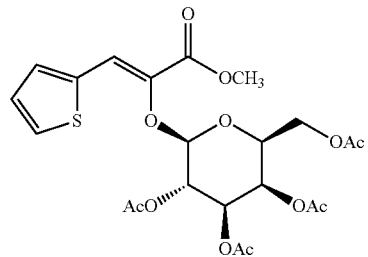 [SMILES: COC(=O)/C(=C/c1cccs1)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-methoxy-3-oxo-1-(thiophen-2-yl)prop-1-en-2-yl)oxy)tetrahydro-2H-pyran-3,4,5-triyl triacetate (C15)

The title compound was prepared as described for C4 using methyl 2-oxo-3-(thiophen-2-yl)propanoate B13 (Otava, 100 mg, 0.543 mmol), sodium hydride (13.03 mg, 0.373 mmol) and 2,3,4,6-tetra-O-acetyl-α-D-galactose bromide (223 mg, 0.543 mmol). The compound was isolated in the form of white solid in 23% yield.

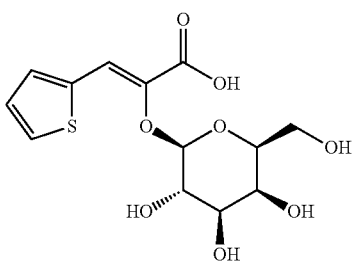 [SMILES: O=C(O)/C(=C/c1cccs1)O[C@H]1O[C@@H](CO)[C@@H](O)[C@@H](O)[C@@H]1O]

(Z)-3-(Thiophen-2-yl)-2-(((2R,3S,4R,5S,6S)-3,4,5-trihydroxy-6-(hydroxymethyl)tetrahydro-2H-pyran-2-yl)oxy)acrylic acid (RX-15)

The title compound was prepared as described for RX-4 to give the product as a brown solid in 98% yield: $^1$H NMR (400 MHz, MeOH-d$_4$): δ 7.40 (d, J=5.1 Hz, 1H), 7.28 (d, J=4.1 Hz, 1H), 7.21 (s, 1H), 6.94 (dd, J=5.1, 3.7 Hz, 1H), 5.21 (d, J=7.8 Hz, 1H), 3.86 (dd, J=9.6, 7.8 Hz, 1H), 3.77 (d, J=3.0 Hz, 1H), 3.55 (m, 2H), 3.45 (dd, J=9.7, 3.4 Hz, 1H), 3.40 (t, J=6.1 Hz, 1H); $^{13}$C NMR (101 MHz, MeOH-d$_4$): δ 166.82, 140.45, 137.54, 131.89, 130.34, 127.58, 120.02, 102.99, 77.18, 75.13, 73.06, 70.12, 62.08; ESI-HRMS m/z: calcd for C$_{13}$H$_{16}$O$_8$SNa$^+$: 355.0459. found 355.0469.

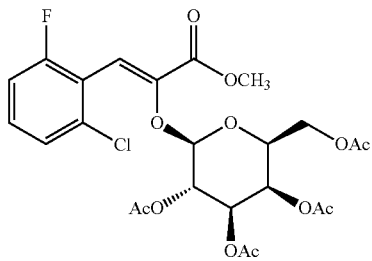 [SMILES: COC(=O)/C(=C/c1c(F)cccc1Cl)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-1-(2-chloro-6-fluorophenyl)-3-methoxy-3-oxoprop-1-en-2-yl)oxy)tetrahydro-2H-pyran-3,4,5-triyl triacetate (C16)

The title compound was prepared as described for C4 using methyl 2-oxo-3-(2-chloro-6-fluorophenyl)propanoate B14 (Otava, 100 mg, 0.434 mmol), sodium hydride (10.41 mg, 0.434 mmol) and 2,3,4,6-tetra-O-acetyl-α-D-galactose bromide (178 mg, 0.434 mmol). The compound was isolated in the form of white solid in 26% yield.

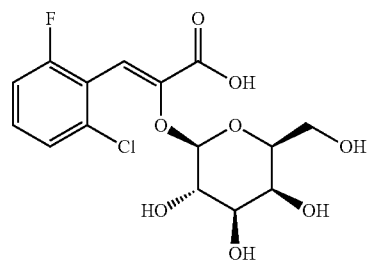 [SMILES: O=C(O)/C(=C/c1c(F)cccc1Cl)O[C@H]1O[C@@H](CO)[C@@H](O)[C@@H](O)[C@@H]1O]

(Z)-3-(2-Chloro-6-fluorophenyl)-2-(((2R,3S,4R,5S,6S)-3,4,5-trihydroxy-6-(hydroxymethyl)tetrahydro-2H-pyran-2-yl)oxy)acrylic acid (RX-16)

The title compound was prepared as described for RX-4 to give the product as a brown solid in quantitative yield: $^1$H NMR (400 MHz, MeOH-d$_4$) δ 7.22 (m, 2H), 6.99 (t, J=8.7 Hz, 1H), 6.92 (s, 1H), 4.52 (d, J=7.4 Hz, 1H), 3.67 (d, J=2.5 Hz, 1H), 3.45 (m, 2H), 3.33-3.24 (m, 2H), 3.11 (m, 1H); ESI-HRMS m/z: calcd for C$_{15}$H$_{16}$ClFO$_8$Na$^+$: 401.0410. found 401.0409.

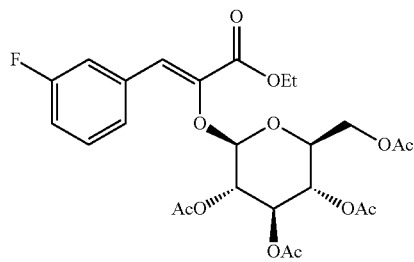 [SMILES: CCOC(=O)/C(=C/c1cccc(F)c1)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-3-ethoxy-1-(3-fluorophenyl)-3-oxoprop-1-en-2-yl)oxy)tetrahydro-2H-pyran-3,4,5-triyl triacetate (C17)

The title compound was prepared as described for C4 using ethyl 3-(3-fluorophenyl)-2-oxopropanoate B5 (100 mg, 0.476 mmol), sodium hydride (13 mg, 0.523 mmol) and 2,3,4,6-tetra-O-acetyl-α-D-glucose bromide (196 mg, 0.476 mmol). The compound was isolated in the form of white solid in 19% yield.

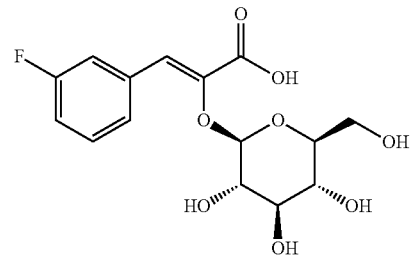 [SMILES: O=C(O)/C(=C/c1cccc(F)c1)O[C@H]1O[C@@H](CO)[C@H](O)[C@@H](O)[C@@H]1O]

(Z)-3-(3-Fluorophenyl)-2-(((2R,3S,4R,5R,6S)-3,4,5-tri hydroxy-6-(hydroxymethyl)tetrahydro-2H-pyran-2-yl)oxy)acrylic acid (RX-17)

The title compound was prepared as described for RX-4 to give the product as a white solid in 92% yield: $^1$H NMR (400 MHz, MeOH-d$_4$): δ 7.69-7.60 (m, 1H), 7.45 (d, J=7.8 Hz, 1H), 7.25 (m, 1H), 6.96 (ddd, J=8.4, 2.6, 0.8 Hz, 1H), 6.92 (s, 1H), 5.17 (d, J=7.6 Hz, 1H), 3.68 (dd, J=12.0, 2.3 Hz, 1H), 3.52 (dd, J=12.0, 5.4 Hz, 1H), 3.32 (m, 3H), 3.15 (m, 1H); $^{13}$C NMR (101 MHz, MeOH-d$_4$): δ 166.78, 164.04 (d, $^1J_{C,F}$=243.2 Hz), 143.86, 137.04 (d, $^3J_{C,F}$=8.5 Hz), 130.90 (d, $^3J_{C,F}$=8.4 Hz), 127.66, 127.63, 124.04, 117.69 (d, $^2J_{C,F}$=23.0 Hz), 116.56 (d, $^2J_{C,F}$=21.7 Hz), 102.68, 78.63, 78.11, 75.69, 71.45, 62.61; ESI-HRMS m/z: calcd for C$_{15}$H$_{17}$FO$_8$Na$^+$: 367.0800. found 367.0800.

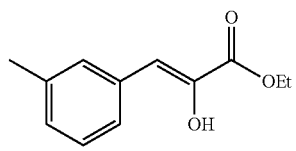

Ethyl (3-methylphenyl)pyruvate (B15)

The title compound was prepared as described for B4 using 3-methylbenzyl bromide (1.250 g, 6.75 mmol), magnesium (0.181 g, 7.43 mmol) and diethyl oxalate (1.974 g, 13.51 mmol). The resulting compound was isolated in the form of colorless oil in 72% yield and use instantly in next step.

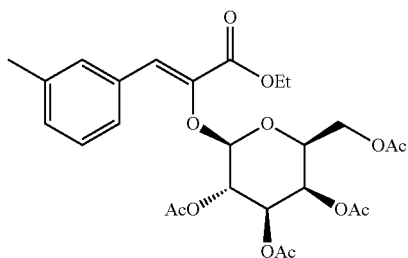 [SMILES: CCOC(=O)/C(=C/c1cccc(C)c1)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-ethoxy-3-oxo-1-(m-tolyl)prop-1-en-2-yl)oxy)tetrahydro-2H-pyran-3,4,5-triyl triacetate (C18)

The title compound was prepared as described for C4 using ethyl 3-(3-methylphenyl)-2-oxopropanoate B15 (100 mg, 0.485 mmol), sodium hydride (11.64 mg, 0.485 mmol) and 2,3,4,6-tetra-O-acetyl-α-D-galactose bromide (199 mg, 0.485 mmol). The compound was isolated in the form of white solid in 25% yield.

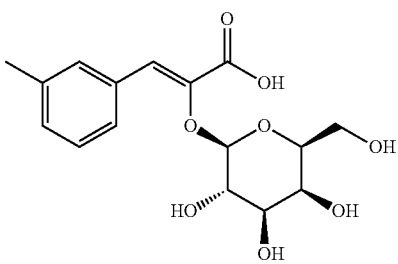 [SMILES: Cc1cccc(/C=C(\O[C@H]2O[C@@H](CO)[C@@H](O)[C@@H](O)[C@@H]2O)C(=O)O)c1]

(Z)-3-(m-Tolyl)-2-(((2R,3S,4R,5S,6S)-3,4,5-trihydroxy-6-(hydroxymethyl)tetrahydro-2H-pyran-2-yl)oxy)acrylic acid (RX-18)

The title compound was prepared as described for RX-4 to give the product as a white solid in 96% yield: $^1$H NMR (400 MHz, MeOH-d$_4$): δ 7.64 (s, 1H), 7.58 (d, J=7.7 Hz, 1H), 7.13 (t, J=7.7 Hz, 1H), 7.03 (d, J=7.6 Hz, 1H), 6.94 (s, 1H), 4.97 (d, J=7.7 Hz, 1H), 3.82-3.69 (m, 2H), 3.61-3.49 (m, 2H), 3.47-3.33 (m, 2H), 2.24 (s, 3H); $^{13}$C NMR (101 MHz, MeOH-d$_4$): δ 167.69, 142.77, 139.05, 134.43, 132.40, 130.83, 129.23, 129.00, 126.37, 103.76, 77.11, 75.02, 73.02, 70.04, 61.99, 21.40; ESI-HRMS m/z: calcd for $C_{16}H_{20}O_8Na^+$: 363.1051. found 363.1055.

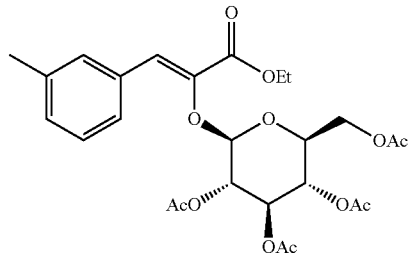 [SMILES: CCOC(=O)/C(=C/c1cccc(C)c1)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-3-ethoxy-3-oxo-1-(m-tolyl)prop-1-en-2-yl)oxy)tetrahydro-2H-pyran-3,4,5-triyl triacetate (C19)

The title compound was prepared as described for C4 using ethyl 3-(3-methylphenyl)-2-oxopropanoate B18 (100 mg, 0.485 mmol), sodium hydride (11.64 mg, 0.485 mmol) and 2,3,4,6-tetra-O-acetyl-α-D-glucose bromide (199 mg, 0.485 mmol). The compound was isolated in the form of white solid in 19% yield.

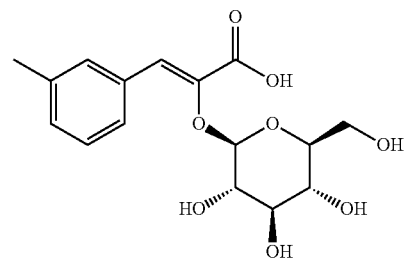 [SMILES: Cc1cccc(/C=C(\O[C@H]2O[C@@H](CO)[C@H](O)[C@@H](O)[C@@H]2O)C(=O)O)c1]

(Z)-3-(m-Tolyl)-2-(((2R,3S,4R,5R,6S)-3,4,5-trihydroxy-6-(hydroxymethyl)tetrahydro-2H-pyran-2-yl)oxy)acrylic acid (RX-19)

The title compound was prepared as described for (RX-4) to give the product as a white solid in quantitative yield: $^1$H NMR (400 MHz, MeOH-d$_4$): δ 7.60 (s, 1H), 7.57 (d, J=7.8 Hz, 1H), 7.14 (t, J=7.7 Hz, 1H), 7.04 (d, J=7.6 Hz, 1H), 6.94 (s, 1H), 5.08 (d, J=7.7 Hz, 1H), 3.66 (dd, J=12.0, 2.3 Hz, 1H), 3.51 (dd, J=12.0, 5.3 Hz, 1H), 3.45-3.23 (m, 3H), 3.16-3.09 (m, 1H), 2.24 (s, 3H); $^{13}$C NMR (101 MHz, MeOH-d$_4$): δ 166.64, 141.90, 138.26, 133.76, 131.51, 130.02, 128.46, 128.08, 125.43, 102.13, 77.71, 77.30, 74.92, 70.62, 61.82, 20.64; ESI-HRMS m/z: calcd for $C_{16}H_{20}O_8Na^+$: 363.1051. found 363.1044.

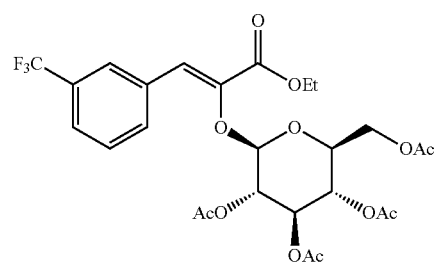 [SMILES: CCOC(=O)/C(=C/c1cccc(C(F)(F)F)c1)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-3-ethoxy-3-oxo-1-(3-(trifluoromethyl)phenyl)prop-1-en-2-yl)oxy)tetrahydro-2H-pyran-3,4,5-triyl triacetate (C20)

The title compound was prepared as described for C4 using ethyl 3-(3-(trifluoromethyl)phenyl)-2-oxopropanoate B10 (100 mg, 0.384 mmol), sodium hydride (10.14 mg, 0.544 mmol) and 2,3,4,6-tetra-O-acetyl-α-D-glucose bromide (158 mg, 0.384 mmol). The resulting compound was isolated in the form of white solid in 22% yield.

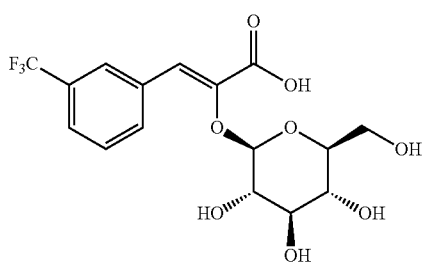 [SMILES: O=C(O)/C(=C/c1cccc(C(F)(F)F)c1)O[C@H]1O[C@@H](CO)[C@H](O)[C@@H](O)[C@@H]1O]

(Z)-3-(3-(Trifluoromethyl)phenyl)-2-(((2R,3S,4R,5R,6S)-3,4,5-trihydroxy-6-(hydroxymethyl)tetrahydro-2H-pyran-2-yl)oxy)acrylic acid (RX-20)

The title compound was prepared as described for RX-4 to give the product as a white solid in 82% yield: $^1$H NMR (400 MHz, MeOH-$d_4$): δ 8.22 (s, 1H), 7.93 (d, J=7.7 Hz, 1H), 7.48 (m, 2H), 7.03 (s, 1H), 5.22 (d, J=7.4 Hz, 1H), 3.70 (dd, J=12.0, 2.2 Hz, 1H), 3.50 (dd, J=12.0, 5.5 Hz, 1H), 3.44-3.31 (m, 2H), 3.28-3.15 (m, 2H); $^{13}$C NMR (101 MHz, MeOH-$d_4$): δ 166.56, 144.23, 135.80, 134.97, 131.79, 131.47, 130.09, 128.00, 126.16, 123.97, 102.69, 78.66, 78.01, 75.72, 71.59, 62.75; ESI-HRMS m/z: calcd for $C_{16}H_{17}F_3O_8Na^+$: 417.0768. found 417.0757.

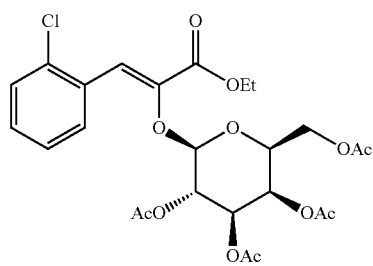 [SMILES: CCOC(=O)/C(=C/c1ccccc1Cl)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-1-(2-chlorophenyl)-3-ethoxy-3-oxoprop-1-en-2-yl)oxy)tetrahydro-2H-pyran-3,4,5-triyl triacetate (C21)

The title compound was prepared as described for C4 using ethyl 3-(2-chlorophenyl)-2-oxopropanoate B11 (100 mg, 0.441 mmol), sodium hydride (11.65 mg, 0.485 mmol) and 2,3,4,6 tetra-O-acetyl-α-D-galactose bromide (181 mg, 0.441 mmol). The resulting compound was isolated in the form of white solid in 36% yield.

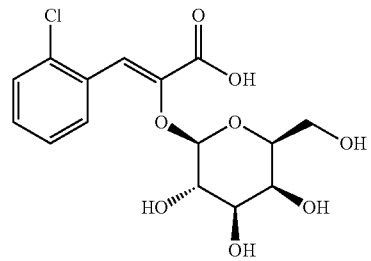

(Z)-3-(2-Chlorophenyl)-2-(((2R,3S,4R,5S,6S)-3,4,5-tri hydroxy-6-(hydroxymethyl)tetrahydro-2H-pyran-2-yl)oxy)acrylic acid (RX-21)

The title compound was prepared as described for RX-4 to give the product as a white solid in 89% yield: $^1$H NMR (400 MHz, MeOH-$d_4$): δ 8.31 (m, 1H), 7.39-7.26 (m, 2H), 7.24-7.13 (m, 2H), 5.07 (d, J=7.7 Hz, 1H), 3.76 (d, J=4.2 Hz, 1H), 3.65 (dd, J=9.7, 7.7 Hz, 1H), 3.62-3.50 (m, 2H), 3.44-3.36 (m, 2H); $^{13}$C NMR (101 MHz, MeOH-$d_4$): δ 166.99, 144.50, 135.13, 133.42, 132.62, 131.03, 130.29, 127.98, 120.52, 103.40, 77.26, 74.98, 72.94, 70.07, 62.02; ESI-HRMS m/z: calcd for $C_{15}H_{17}ClO_8Na^+$: 383.0505. found 383.0495.

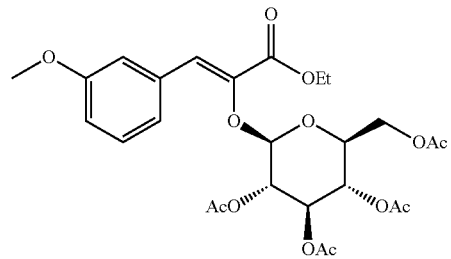 [SMILES: CCOC(=O)/C(=C/c1cccc(OC)c1)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-3-ethoxy-1-(3-methoxyphenyl)-3-oxoprop-1-en-2-yl)oxy)tetrahydro-2H-pyran-3,4,5-triyl triacetate (C22)

The title compound was prepared as described for C4 using ethyl 3-(3-methoxyphenyl)-2-oxopropanoate B9 (100 mg, 0.369 mmol), sodium hydride (11.88 mg, 0.495 mmol) and 2,3,4,6 tetra-O-acetyl-α-D-glucose bromide (185 mg, 0.450 mmol). The resulting compound was isolated in the form of white solid in 22% yield.

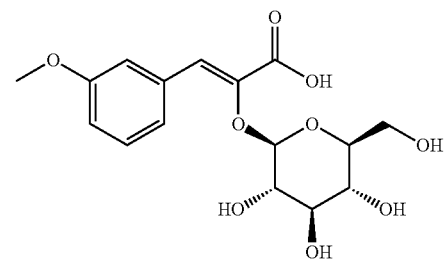 [SMILES: COc1cccc(/C=C(\O[C@H]2O[C@@H](CO)[C@H](O)[C@@H](O)[C@@H]2O)C(=O)O)c1]

(Z)-3-(3-Methoxyphenyl)-2-(((2R,3S,4R,5R,6S)-3,4,5-trihydroxy-6-(hydroxymethyl)tetrahydro-2H-pyran-2-yl)oxy)acrylic acid (RX-22)

The title compound was prepared as described for RX-4 to give the product as a white solid in 84% yield: $^1$H NMR (400 MHz, MeOH-$d_4$): δ 7.58-7.53 (m, 1H), 7.24-7.11 (m, 2H), 6.94 (s, 1H), 6.79 (ddd, J=7.4, 2.5, 1.9 Hz, 1H), 5.14 (d, J=7.6 Hz, 1H), 3.72 (s, 3H), 3.67 (dd, J=12.0, 2.4 Hz, 1H), 3.52 (dd, J=12.0, 5.3 Hz, 1H), 3.43-3.23 (m, 3H), 3.14 (m, 1H); $^{13}$C NMR (101 MHz, MeOH-$d_4$): δ 167.18, 160.95, 142.87, 135.93, 130.17, 125.92, 124.47, 116.70, 115.89, 102.78, 78.57, 78.10, 75.82, 71.46, 62.57, 55.84; ESI-HRMS m/z: calcd for $C_{16}H_{20}O_9Na^+$: 379.1000. found 379.1007.

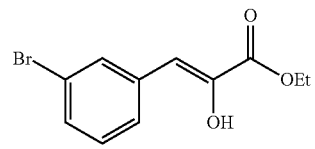

Ethyl (2-bromophenyl)pyruvate (B16)

The title compound was prepared as described for B4 using 3-bromobenzyl bromide (1.250 g, 5.00 mmol), magnesium (0.134 g, 5.50 mmol) and diethyl oxalate (1.462 g, 10.00 mmol). The product was isolated in the form of colorless oil in 80% yield and use instantly in next step.

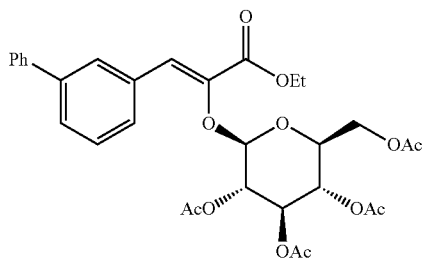 [SMILES: CCOC(=O)/C(=C/c1cccc(-c2ccccc2)c1)O[C@H]1O[C@@H](COC(C)=O)[C@H](OC(C)=O)[C@@H](OC(C)=O)[C@@H]1OC(C)=O]

(2R,3S,4R,5S,6S)-2-(((Z)-1-([1,1'-Biphenyl]-3-yl)-3-ethoxy-3-oxoprop-1-en-2-yl)oxy)-6-(acetoxymethyl)tetrahydro-2H-pyran-3,4,5-triyl triacetate (C23)

The title compound was prepared as described for C4 using ethyl 3-(3-arylphenyl)-2-oxopropanoate (B14) (100 mg, 0.373 mmol), sodium hydride (9.0 mg, 0.373 mmol) and 2,3,4,6-tetra-O-acetyl-α-D-glucose bromide (153 mg, 0.373 mmol). The compound was isolated in the form of white solid in 16% yield.

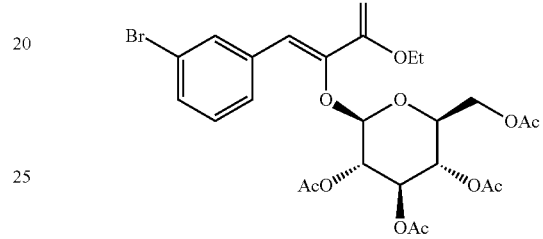

(2S,3S,4R,5S,6R)-2-(Acetoxymethyl)-6-(((Z)-1-(3-bromophenyl)-3-ethoxy-3-oxoprop-1-en-2-yl)oxy)tetrahydro-2H-pyran-3,4,5-triyl triacetate (C24)

The title compound was prepared as described for C4 using Ethyl 3-(3-bromophenyl)-2-oxopropanoate B16 (100 mg, 0.369 mmol), sodium hydride (9.74 mg, 0.406 mmol) and 2,3,4,6 tetra-O-acetyl-α-D-glucose bromide (152 mg, 0.369 mmol). The resulting compound was isolated in the form of white solid in 24% yield.

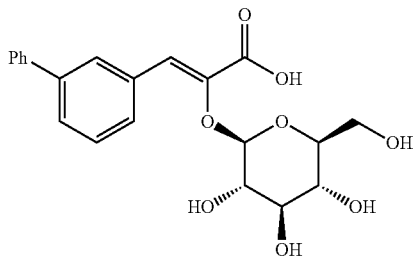 [SMILES: O=C(O)/C(=C/c1cccc(-c2ccccc2)c1)O[C@H]1O[C@@H](CO)[C@H](O)[C@@H](O)[C@@H]1O]

(Z)-3-([1,1'-Biphenyl]-3-yl)-2-(((2R,3S,4R,5R,6S)-3,4,5-trihydroxy-6-(hydroxymethyl)tetrahydro-2H-pyran-2-yl)oxy)acrylic acid (RX-23)

The title compound was prepared as described for RX-4 to give the product as a white solid in 91% yield: $^1$H NMR (400 MHz, MeOH-$d_4$): δ 8.27 (s, 1H), 7.75 (d, J=7.7 Hz, 1H), 7.70-7.64 (m, 2H), 7.58 (d, J=8.4 Hz, 1H), 7.44 (m, 3H), 7.33 (m, 1H), 7.13 (s, 1H), 5.25 (d, J=7.6 Hz, 1H), 3.77 (dd, J=12.0, 2.3 Hz, 1H), 3.60 (dd, J=12.0, 5.5 Hz, 1H), 3.55-3.33 (m, 3H), 3.29-3.22 (m, 1H); ESI-HRMS m/z: calcd for $C_{21}H_{22}O_8Na^+$: 425.1207. found 425.1205.

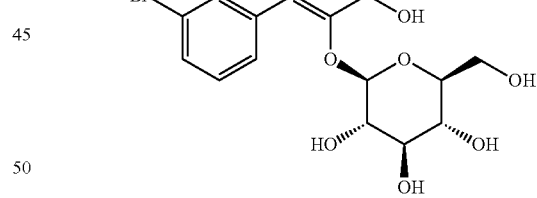

(Z)-3-(3-Bromophenyl)-2-(((2R,3S,4R,5R,6S)-3,4,5-trihydroxy-6-(hydroxymethyl)tetrahydro-2H-pyran-2-yl)oxy)acrylic acid (RX-24)

The title compound was prepared as described for RX-4 to give the product as a white solid in quantitative yield: $^1$H NMR (400 MHz, MeOH-$d_4$): δ 8.03 (t, J=1.8 Hz, 1H), 7.66 (d, J=7.8 Hz, 1H), 7.34 (m, 1H), 7.16 (t, J=7.9 Hz, 1H), 6.83 (s, 1H), 5.13 (d, J=7.5 Hz, 1H), 3.69 (dd, J=12.0, 2.3 Hz, 1H), 3.53 (dd, J=12.0, 5.5 Hz, 1H), 3.41-3.22 (m, 3H), 3.16 (m, 1H); $^{13}$C NMR (101 MHz, MeOH-$d_4$): δ 167.62, 145.44, 137.31, 133.97, 132.36, 130.97, 130.17, 123.19, 122.68, 102.89, 78.66, 78.17, 75.73, 71.49, 62.75; ESI-HRMS m/z: calcd for $C_{15}H_{17}BrO_8Na^+$: 427.0000. found 427.0011.

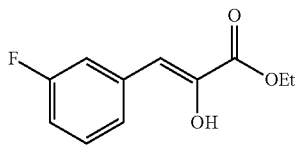 [SMILES: CCOC(=O)/C(O)=C/c1cccc(F)c1]

Ethyl (3-fluorophenyl)pyruvate (B17)

The title compound was prepared as described for B4 using 3-bromobenzyl bromide (1.250 g, 5.00 mmol), magnesium (0.134 g, 5.50 mmol) and diethyl oxalate (1.462 g, 10.00 mmol). The product was isolated in the form of colorless oil in 80% yield and use instantly in next step.

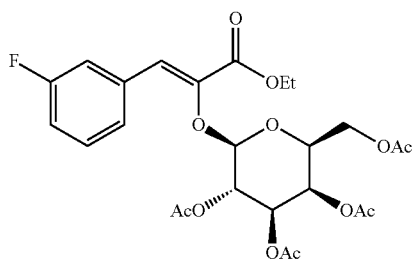 [SMILES: CCOC(=O)/C(=C/c1cccc(F)c1)O[C@H]1O[C@@H](COC(C)=O)[C@@H](OC(C)=O)[C@@H](OC(C)=O)[C@@H]1OC(C)=O]

(2S,3R,4R,5S,6R)-2-(Acetoxymethyl)-6-(((Z)-3-ethoxy-1-(3-fluorophenyl)-3-oxoprop-1-en-2-yl)oxy)tetrahydro-2H-pyran-3,4,5-triyl triacetate (C25)

The title compound was prepared as described for C4 using Ethyl 3-(3-bromophenyl)-2-oxopropanoate B17 (100 mg, 0.369 mmol), sodium hydride (9.74 mg, 0.406 mmol) and 2,3,4,6-tetra-O-acetyl-α-D-galactose bromide (152 mg, 0.369 mmol). The resulting compound was isolated in the form of white solid in 24% yield.

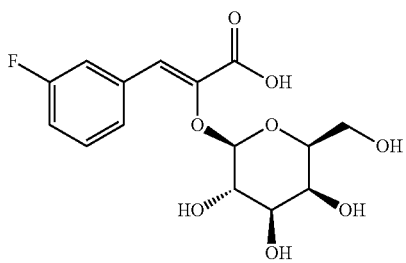 [SMILES: O=C(O)/C(=C/c1cccc(F)c1)O[C@H]1O[C@@H](CO)[C@@H](O)[C@@H](O)[C@@H]1O]

(Z)-3-(3-Fluorophenyl)-2-(((2R,3S,4R,5S,6S)-3,4,5-trihydroxy-6-(hydroxymethyl)tetrahydro-2H-pyran-2-yl)oxy)acrylic acid (RX-25)

The title compound was prepared as described for RX-4 to give the product as a white solid in 98% yield: $^1$H NMR (400 MHz, MeOH-$d_4$) δ 7.98 (t, J=1.7 Hz, 1H), 7.75 (d, J=7.9 Hz, 1H), 7.39-7.33 (m, 1H), 7.16 (t, J=7.9 Hz, 1H), 6.89 (s, 1H), 5.06 (d, J=7.7 Hz, 1H), 3.81-3.69 (m, 2H), 3.57 (ddd, J=29.4, 11.2, 6.2 Hz, 2H), 3.41 (m, 2H); ESI-HRMS m/z: calcd for $C_{15}H_{17}BrO_8Na^+$: 427.0000. found 427.8897.

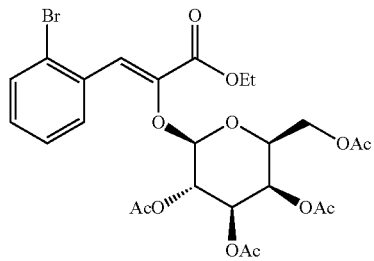

(2S,3R,4R,5S,6R)-2-(Acetoxymethyl)-6-(((Z)-1-(2-bromophenyl)-3-ethoxy-3-oxoprop-1-en-2-yl)oxy)tetrahydro-2H-pyran-3,4,5-triyl triacetate (C26)

The title compound was prepared as described for C4 using ethyl 3-(2-bromophenyl)-2-oxopropanoate B8 (100 mg, 0.369 mmol), sodium hydride (9.74 mg, 0.406 mmol) and 2,3,4,6-tetra-O-acetyl-α-D-galactose bromide (152 mg, 0.369 mmol). The resulting compound was isolated in the form of white solid in 24% yield.

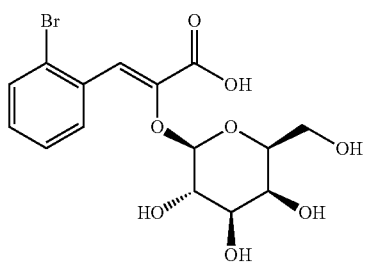 [SMILES: O=C(O)/C(=C/c1ccccc1Br)O[C@H]1O[C@@H](CO)[C@@H](O)[C@@H](O)[C@@H]1O]

(Z)-3-(2-Bromophenyl)-2-(((2R,3S,4R,5S,6S)-3,4,5-trihydroxy-6-(hydroxymethyl)tetrahydro-2H-pyran-2-yl)oxy)acrylic acid (RX-26)

The title compound was prepared as described for RX-4 to give the product as a white solid in quantitative yield: $^1$H NMR (400 MHz, MeOH-$d_4$) δ 8.26 (dd, J=7.8, 1.6 Hz, 1H), 7.50 (dd, J=8.1, 1.2 Hz, 1H), 7.29-7.21 (m, 2H), 7.13-7.06 (m, 1H), 5.05 (d, J=7.7 Hz, 1H), 3.76 (d, J=2.6 Hz, 1H), 3.67-3.49 (m, 3H), 3.39 (m, 2H); ESI-HRMS m/z: calcd for $C_{15}H_{17}BrO_8Na^+$: 427.0000. found 427.0012.

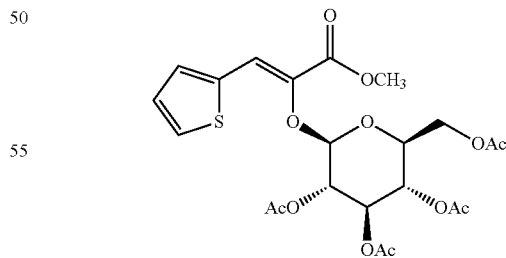

(2S,3S,4R,5S,6R)-2-(Acetoxymethyl)-6-(((Z)-3-methoxy-3-oxo-1-(thiophen-2-yl)prop-1-en-2-yl)oxy)tetrahydro-2H-pyran-3,4,5-triyl triacetate (C27)

The title compound was prepared as described for C4 using methyl 2-oxo-3-(thiophen-2-yl)propanoate B15

(Otava, 100 mg, 0.543 mmol), sodium hydride (13.03 mg, 0.373 mmol) and 2,3,4,6-tetra-O-acetyl-α-D-glucose bromide (223 mg, 0.543 mmol). The compound was isolated in the form of white solid in 18% yield.

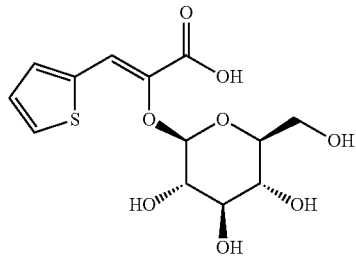 [SMILES: O=C(O)/C(=C/c1cccs1)O[C@H]1O[C@@H](CO)[C@H](O)[C@@H](O)[C@@H]1O]

(Z)-3-(Thiophen-2-yl)-2-(((2R,3S,4R,5R,6S)-3,4,5-trihydroxy-6-(hydroxymethyl)tetrahydro-2H-pyran-2-yl)oxy)acrylic acid (RX-27)

The title compound was prepared as described for RX-4 to give the product as a brown solid in 84% yield: $^1$H NMR (400 MHz, MeOH-d$_4$) δ 7.42 (dd, J=4.3, 0.9 Hz, 1H), 7.29-7.22 (m, 2H), 6.95 (dd, J=5.1, 3.8 Hz, 1H), 5.31 (d, J=7.8 Hz, 1H), 3.67 (dd, J=12.1, 2.3 Hz, 1H), 3.53 (ddd, J=26.3, 10.6, 6.7 Hz, 2H), 3.36-3.23 (m, 2H), 3.18-3.12 (m, 1H); ESI-HRMS m/z: calcd for C$_{13}$H$_{16}$O$_8$SNa$^+$: 355.0459. found 355.0443.

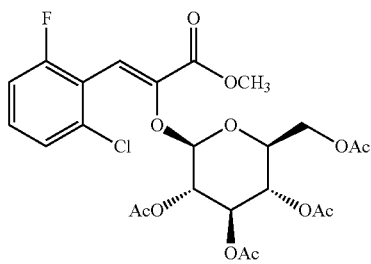 [SMILES: COC(=O)/C(=C/c1c(F)cccc1Cl)O[C@H]1O[C@@H](COC(C)=O)[C@H](OC(C)=O)[C@@H](OC(C)=O)[C@@H]1OC(C)=O]

(2S,3S,4R,5S,6R)-2-(Acetoxymethyl)-6-(((Z)-1-(2-chloro-6-fluorophenyl)-3-methoxy-3-oxoprop-1-en-2-yl)oxy)tetrahydro-2H-pyran-3,4,5-triyl triacetate (C28)

The title compound was prepared as described for C4 using methyl 3-(2-chloro-6-fluorophenyl)-2-oxopropanoate B16 (100 mg, 0.434 mmol), sodium hydride (10.41 mg, 0.434 mmol) and 2,3,4,6-tetra-O-acetyl-α-D-glucose bromide (178 mg, 0.434 mmol). The compound was isolated in the form of white solid in 8% yield.

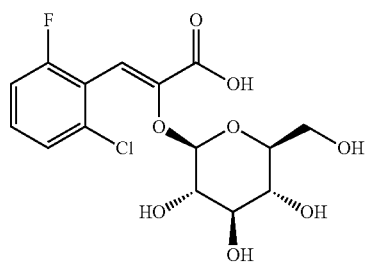 [SMILES: O=C(O)/C(=C/c1c(F)cccc1Cl)O[C@H]1O[C@@H](CO)[C@H](O)[C@@H](O)[C@@H]1O]

(Z)-3-(2-Chloro-6-fluorophenyl)-2-(((2R,3S,4R,5R,6S)-3,4,5-trihydroxy-6-(hydroxymethyl)tetrahydro-2H-pyran-2-yl)oxy)acrylic acid (RX-28)

The title compound was prepared as described for RX-4 to give the product as a white solid in 94% yield: $^1$H NMR (400 MHz, MeOH-d$_4$): δ 7.28-7.15 (m, 2H), 7.01 (t, J=8.2 Hz, 1H), 6.88 (s, 1H), 4.67 (d, J=6.7 Hz, 1H), 3.47 (qd, J=11.9, 3.6 Hz, 2H), 3.19-3.11 (m, 3H), 2.89-2.81 (m, 1H); $^{13}$C NMR (101 MHz, MeOH-d$_4$): δ 165.61, δ 160.88 (d, $^1J_{C,F}$=251.8 Hz), 145.81, 134.89 (d, $^3J_{C,F}$=5.0 Hz), 130.59 (d, $^3J_{C,F}$ J=9.5 Hz), 125.13 (d, $^3J_{C,F}$=3.5 Hz), 121.77 (d, $^2J_{C,F}$=19.6 Hz), 115.22, 1114.58 (d, $^2J_{C,F}$=22.7 Hz, 102.59, 77.22, 76.96, 74.41, 70.18, 61.47; ESI-HRMS m/z: calcd for C$_{15}$H$_{16}$ClFO$_8$Na$^+$: 401.0410. found 401.0407.

Synthesis of intermediate methyl (4-bromophenyl)pyruvate (B18)

The synthesized was performed by a route corresponding to the one described by Busca et al. (Org. Bioorg. Chem. 2004, 2, 2684-2691).

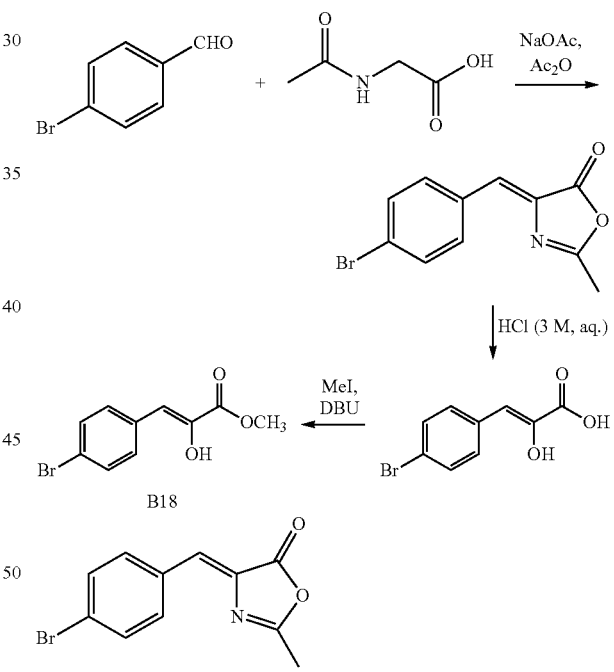

4-(4-Bromobenzylidene)-2-methyloxazol-5(4H)-one

A mixture of 4-bromo-benzaldehyde (2.88 g, 35.10 mmol), N-acetyl-glycine (3.80 g, 32.40 mmol) and sodium acetate (2.88 g, 35.1 mmol) in acetic anhydride (13.79 g, 135 mmol), was refluxed for 1 h with continuous stirring. After cooling, the reaction was quenched with ice and vigorously stirred for 1 h in an ice bath to allow precipitation. Filtration afforded compound in 64% yield.

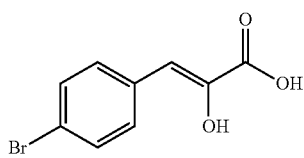 [SMILES: O=C(O)/C(O)=C/c1ccc(Br)cc1]

3-(4-Bromophenyl)-2-hydroxyacrylic acid

A suspension of 4-(4-bromobenzylidene)-2-methyloxazol-5(4H)-one (1.00 g, 3.76 mmol) in 3 M aqueous hydrochloric acid (3 mL, 9.00 mmol) was stirred at reflux for 3 h. The reaction mixture was cooled to reach at room temperature to allow crystallization. Filtration afforded the title compound in 72% yield.

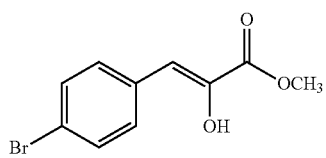 [SMILES: COC(=O)/C(O)=C/c1ccc(Br)cc1]

Methyl (4-bromophenyl)pyruvate (B18)

To a solution of 3-(4-bromophenyl)-2-oxopropionic acid (70.0 mg, 0.288 mmol) in DMF (2 mL) at 0° C. was added DBU (72.2 mg, 0.288 mmol) and iodomethane (204 mg, 1.440 mmol). The reaction mixture was stirred for 2.5 hours at the same temperature. The reaction was acidified with 1 M HCl and extraction with ether (3×25 mL), drying (MgSO$_4$), concentrated under reduced pressure and dried on vacuum to get the light brown oily compound B18 in 68% yield and used as such in next step.

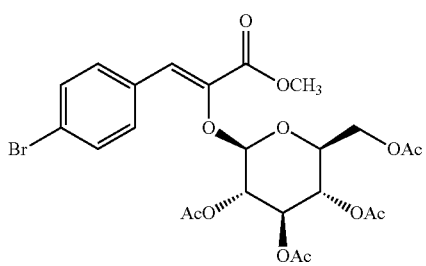

(2S,3S,4R,5S,6R)-2-(Acetoxymethyl)-6-(((Z)-1-(4-bromophenyl)-3-methoxy-3-oxoprop-1-en-2-yl)oxy)tetrahydro-2H-pyran-3,4,5-triyl triacetate (C29)

The title compound was prepared as described for C4 using methyl 3-(4-bromophenyl)-2-oxopropanoate B18 (100 mg, 0.389 mmol), sodium hydride (10.27 mg, 0.428 mmol) and 2,3,4,6-tetra-O-acetyl-α-D-glucose bromide (160 mg, 0.389 mmol). The resulting compound was isolated in the form of white solid in 34% yield.

RX29

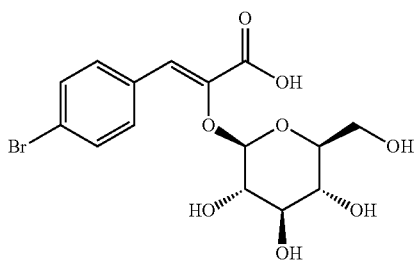

(Z)-3-(4-Bromophenyl)-2-(((2R,3S,4R,5R,6S)-3,4,5-tri hydroxy-6-(hydroxymethyl)tetrahydro-2H-pyran-2-yl)oxy)acrylic acid (RX-29)

The title compound was prepared as described for RX-4 to give the product as a white solid in 94% yield: $^1$H NMR (400 MHz, MeOH-d$_4$) δ 7.69 (d, J=8.5 Hz, 2H), 7.41 (d, J=8.6 Hz, 2H), 6.91 (s, 1H), 5.12 (d, J=7.5 Hz, 1H), 3.66 (dd, J=12.0, 2.3 Hz, 1H), 3.52 (dd, J=12.0, 5.2 Hz, 1H), 3.32 (m, 3H), 3.17-3.11 (m, 1H); ESI-HRMS m/z: calcd for C$_{15}$H$_{17}$BrO$_8$Na$^+$: 427.0000. found 427.0016.

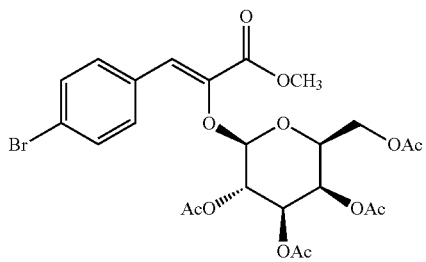

(2S,3R,4R,5S,6R)-2-(Acetoxymethyl)-6-(((Z)-1-(4-bromophenyl)-3-methoxy-3-oxoprop-1-en-2-yl)oxy)tetrahydro-2H-pyran-3,4,5-triyl triacetate (C30)

The title compound was prepared as described for C4 using methyl 3-(4-bromophenyl)-2-oxopropanoate B18 (100 mg, 0.389 mmol), sodium hydride (10.27 mg, 0.428 mmol) and 2,3,4,6-tetra-O-acetyl-α-D-galactose bromide (160 mg, 0.389 mmol). The resulting compound was isolated in the form of white solid in 11% yield.

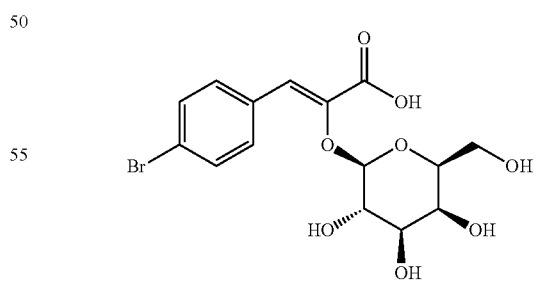

(Z)-3-(4-Bromophenyl)-2-(((2R,3S,4R,5S,6S)-3,4,5-trihydroxy-6-(hydroxymethyl)tetrahydro-2H-pyran-2-yl)oxy)acrylic acid (RX-30)

The title compound was prepared as described for RX-4 to give the product as a white solid in 96% yield: $^1$H NMR (400 MHz, MeOH-d$_4$) δ 7.71 (d, J=8.6 Hz, 2H), 7.39 (d, J=8.6 Hz, 2H), 6.90 (s, 1H), 5.03 (d, J=7.7 Hz, 1H), 3.78-3.67 (m, 2H), 3.55 (ddd, J=28.8, 11.2, 6.2 Hz, 2H), 3.46-3.36 (m, 2H); ESI-HRMS m/z: calcd for C$_{15}$H$_{17}$BrO$_8$Na$^+$: 427.0000. found 427.0017.

The invention is further illustrated by the following examples.

Example 1

3-Phenyl-2-(3,4,5-trihydroxy-6-hydroxymethyl-tetrahydro-pyran-2-yloxy)-acrylic acid (RX1)

The enolic glucoside of phenylpyruvic acid (here RX1) was isolated by solvent extraction followed by SPE and semi-preparative HPLC from a batch of rooibos (*Aspalathus linearis*). Alternatively, the compound can be isolated as described by Marais et al (Tetrahedron Letters, 1996).

As shown in FIG. 1 RX1 is able to reduce the blood sugar of monkeys for prolonged periods of time. FIG. 1 shows reduction in plasma glucose level of a diabetic primate M1081 (baseline glucose 6.3 mmol/L) over 6 h after a single dose of RX1 (tested at ca. 70.5 ug/6.78 kg animal=10.4 ug/kg BW).

Example 2

Figure 2:
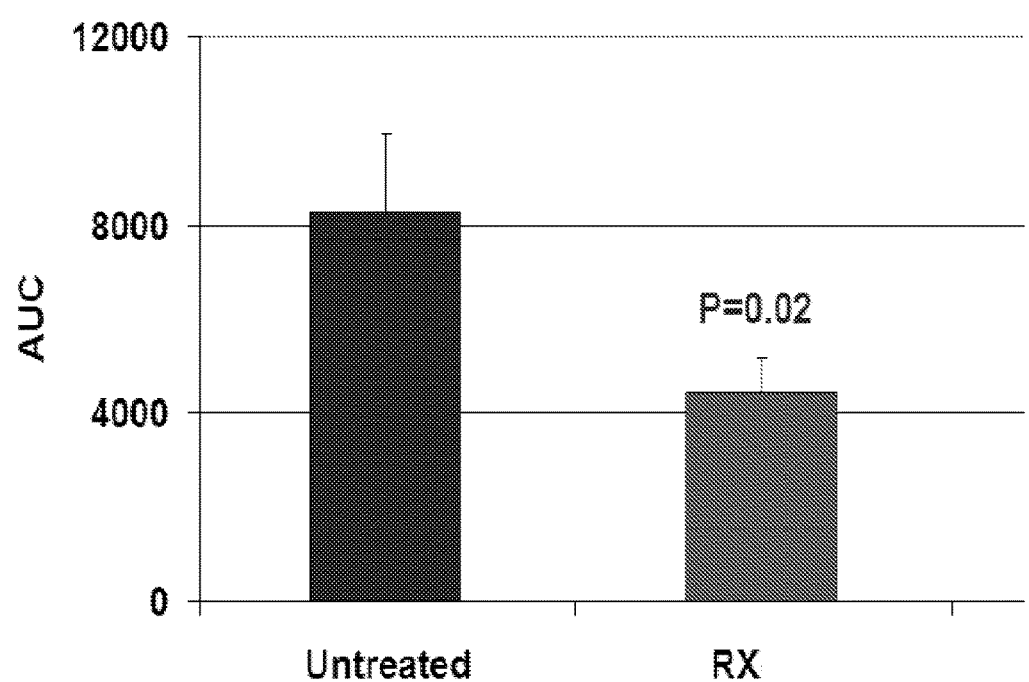
FIG. 2 is a graphical representation of glucose stimulated insulin secretion rate AUC values comparing untreated and RX-1 treated prediabetic monkeys.

Glucose Stimulated Insulin Secretion Rate AUC Values of Untreated and RX-1 Treated Prediabetic Monkeys Prediabetic vervet monkeys (fasting plasma glucose levels between 4.0 and 5.5 mM) were treated with 10 ug/kg RX-1 3 times daily with meals for 7 days. Blood samples were collected following 1.75 g/kg oral glucose stimulation at 0, 5, 10, 15, 30, 60, 90, 120 and 180 minutes. AUC values calculated mean glucose stimulated insulin secretion values over the time interval 0-120 min. Four monkeys were used in each group (untreated, RX1-treated). As appears from FIG. 2 RX-1 treatment decreased insulin secretion by 46% while achieving a better glycaemic control.

Example 3

Glucose Uptake in a Transformed 3T3-L1 Adipocytes

3T3-L1 cells were transformed in culture using modified DMEM differentiation media supplemented with insulin, dexametasone and isobutylmethylxanthine and cultured for 3 days. The transformed 3T3-L1 adipocytes were then cultured for a further 5 days in modified DMEM supplemented with 10% FCS before being exposed to insulin, metformin and compounds of the present invention (see Table 1). Glucose uptake over a three (3) hour period was determined after the 5 days of treatment using a colourometric glucose oxidase method (Biovision Inc, USA).

Table 1 shows the glucose uptake data of 3T3-L1 adipose cells following two (2) days of pre-sensitization with the relevant extracts, followed by a three (3) hour glucose uptake assay with media containing 8 mM glucose. The glucose concentration column represents the glucose concentration remaining in the media following three (3) hour exposure to the cells. The glucose uptake column represents glucose uptake from the media after a 3 hour exposure. SD represents the standard deviation. The percentage increases calculated from the relevant solvent vehicle and the P=values are reflected in the last two columns respectively.

The 3T3-L1 adipose cell glucose uptake assay showed that 3-Phenyl-2-(3,4,5-trihydroxy-6-hydroxymethyl-tetrahydro-pyran-2-yloxy)-acrylic acid (RX-1), (2R,3R,4S,5R,6S)-2-(Acetoxymethyl)-6-((Z)-3-methoxy-3-oxo-1-phenyl-prop-1-en-2-yloxy)tetrahydro-2H-pyran-3,4,5-triyl triacetate (RX-1-triacetate), and (Z)-Methyl 3-phenyl-2-((2S,3R,4S,5S,6R)-3,4,5-trihydroxy-6-(hydroxymethyl) tetra hydro-2H-pyran-2-yloxy)acrylate (RX-1 acrylate) significantly increased the glucose uptake over a 3 hour culture period.

TABLE 1

3T3-L1 Adipose Cell: Glucose Uptake Data

| | Glucose conc. (nM/ul) | SD | Glucose Uptake (nM/ul) | % uptake |
|---|---|---|---|---|
| DMSO (vehicle) | 3.81 | 0.10 | 2.33 | 100.00 |
| Insulin | 2.86 | 0.17 | 3.13 | 134.03 |
| Metformin | 3.27 | 0.12 | 2.73 | 117.14 |
| RX-1 | 3.19 | 0.27 | 2.86 | 122.64 |
| RX-1 triacetate | 2.92 | 0.09 | 3.05 | 130.78 |
| RX-1 acrylate | 2.82 | 0.23 | 3.16 | 135.53 |

Example 4

Analysis of Glucose-Lowering Properties of Rx-1 in Obese, Insulin Resistant Wistar Rats The aim of the study was to determine whether the glucose-lowering properties of Rx-1 is related to the expression of genes involved in glucose uptake, insulin signalling, fatty acid oxidation, cytokine signalling and the glucagon receptor in liver and muscle, and the expression of genes involved in glucagon processing, insulin expression and transcription factors important for β-cell development in the pancreas.

Methods & Results

Three week old male rats were fed a high fat diet for 24 weeks to induce obesity and insulin resistance. Thereafter, rats were treated with 0.3 mg/kg Rx-1 daily for two weeks, and then with 3 mg/kg Rx-1 daily for seven days. Fasting glucose concentrations were measured before treatment, after two weeks treatment with 0.3 mg/kg Rx-1 and then again after seven days treatment with 3 mg/kg Rx-1. After treatment with 3 mg/kg Rx-1 rats were terminated and liver, muscle and pancreas biopsies were taken. Quantitative real-time PCR was used to measure the expression of 12 genes in liver and muscle samples, and ten genes in pancreas samples.

Rats were housed at the Primate Unit (Medical Research Council, South Africa). Rat management including feeding, glucose measurements and terminations, were done according to standard operating procedures (Diabetes Discovery Platform, Medical Research Council). Briefly, three week old rats were fed a high fat diet for 24 weeks to induce T2D. The study group consisted of thirteen rats, eight rats were treated by daily gavage with 0.3 mg/kg Rx-1 for two weeks, and then with 3 mg/kg Rx-1 for seven days. Five rats were used as controls and were treated with water only for three weeks. Rats were terminated after treatment and liver, muscle and pancreas tissue harvested and stored in RNalater (Ambion) as recommended by the manufacturer. The study was approved by the ethics committee of the Medical Research Council of South Africa.

RNA Extraction from Liver Tissue

Tissue was removed from RNAlater, weighed (80-100 mg), and placed in a 2 ml microfuge tube containing 1 ml of Trizol (Invitrogen) and a stainless steel bead (Qiagen). Tissue was homogenised in the TissueLyser (Qiagen) at 25 Hz for 6 min, centrifuged at 12,000 g for 10 min at 4° C., and the supernatant removed and incubated at room temperature for 5 min. Thereafter, 0.2 ml of chloroform (Sigma) was added, shaken vigorously for 15 sec, and then incubated at room temperature for 3 min with occasional mixing. Samples were centrifuged 12,000 g for 15 min at 4° C. and the aqueous phase was transferred to a new tube. RNA was precipitated by adding 0.5 ml isopropanol, mixed well for 30 sec, and placed at −20° C. overnight. The following day, tubes were centrifuged at 12,000 g for 20 min at 4° C. The pellet was washed with 1 ml of 75% ethanol and centrifuged at 12,000 g for 15 min at 4° C. The wash step was repeated. After the second wash, the pellet was air dried by placing tubes with their lids open (on ice) in a PCR cabinet for 2 hours. Excess liquid was removed by blotting tubes on paper towel occasionally during this incubation. The pellet was resuspended by adding 100 µl RNase-free water and incubating at 55° C. for 10 min. RNA concentrations were determined using a spectrophotometer (Nanodrop Technologies). Thereafter, RNA was purified with the RNeasy Mini Kit according to the manufacturer's instructions (Qiagen) and concentrations again determined with the Nanodrop. Genomic DNA was removed by treating RNA with Turbo DNA-free DNase (Ambion) and incubating at 37° C. for 90 min according to the manufacturer's instructions, but using 1.5× the units of DNase and incubation time recommended by the kit. In brief, 20 µg RNA was incubated with 1.5 µl (3 units) DNase, 5 µl DNase buffer, and nuclease-free water in a final reaction volume of 50 µl for 45 min at 37° C., thereafter, another 3 units of DNase was added and incubated for a further 45 min. DNase was inactivated by adding ⅕ volume (10 µl) of the DNase inactivation reagent supplied with the kit. Reactions were incubated at room temperature for 2 min, and centrifuged at 14,000 rpm for 1.5 min. The supernatant was removed and RNA concentrations were measured using the Nanodrop. The quality of the DNase-treated RNA was determined with the RNA 6000 Nano kit using the 2100 Bioanalyser Lab-on-a-Chip system as recommended by the manufacturers (Agilent technologies).

Reverse Transcription

RNA extracted from liver, muscle and pancreas tissue was converted to cDNA using the High Capacity Reverse Transcription kit as recommended by the manufacturers (Applied Biosystems). In brief, 2 µg of DNase-treated RNA was added to nuclease-free water in a volume of 10 µl. Thereafter, 2 µl reaction buffer, 0.8 µl dNTPs, 2 µl random primers, 1 µl RNase-inhibitor, 1 µl reverse transcriptase, and 3.2 µl nuclease-free water were added. The same reaction without the reverse transcription enzyme (minus RT reaction) was set-up to investigate genomic DNA contamination. Reactions were incubated at 25° C. for 10 min, 37° C. for 120 min, and 85° C. for 5 s to inactivate the reverse transcriptase. cDNA samples were stored at −20° C. until expression analysis.

Quantitative Real-Time PCR, Data Collection and Evaluation

The extent of genomic DNA contamination was investigated by performing qRT-PCR of the RT reactions. Undiluted cDNA (plus and minus RT reactions) prepared from liver, muscle, and pancreas were mixed with 12.5 µl SYBR Green mix (Applied Biosystems), 2.25 µl 10 µM Gapdh Forward Primer (900 nM), 2.25 µl 10 µM Gapdh Reverse Primer (900 nM), and H$_2$O in a final volume of 25 µl. After all the reagents had been added, the PCR tubes were briefly spun to ensure that all solutions were at the bottom of the tubes. The PCR reactions were conducted on the ABI 7500 Sequence Detection System Instrument (Applied Biosystems) using the Absolute Quantification (AQ) Software (SDS V1.4), and labelling all samples as unknowns. Universal cycling conditions; 50° C. for 2 min and 95° for 10 min, followed by 40 cycles of 95° C. for 15 s and 60° C. for 1 min were used. A dissociation curve was added. Data was acquired during the extension step (60° C. for 1 min). After the run, default settings for the threshold cycle ($C_T$) and baseline were used and Ct values were exported to Excel for analysis.

For analysis of gene expression, 25 ng of cDNA prepared from liver, muscle and pancreas was mixed with 12.5 µl Taqman universal PCR master mix (Applied Biosystems), 1.25 µl gene-specific primer and probe mixtures (predeveloped Taqman gene expression assays, Applied Biosystems), and H$_2$O in a final volume of 25 µl. The Taqman assays that were used are listed in Table 1. The suffix _m represents an assay whose probe spans an exon-exon junction of the associated gene and therefore will not detect genomic DNA, while the suffix _s represents an assay whose primers and probes are designed within a single exon, such assays will detect genomic DNA.

The PCR reactions were conducted on the ABI 7500 Sequence Detection System Instrument (Applied Biosystems) using universal cycling conditions as described before. All samples were run in duplicate. Data generated on the ABI 7500 Instrument were analysed with the ABI Relative Quantitation (RQ) software (SDS V1.4) using a Ct threshold of 0.1. Relative expression levels were determined by using the $2^{-\Delta\Delta Ct}$ method, where $\Delta\Delta Ct = (Ct_{gene\ studied} - Ct_{housekeeping\ gene})_{treated} - (Ct_{gene\ studied} - Ct_{housekeeping\ gene})_{control}$. The gene expression was normalised to housekeeping genes to correct for differences in cDNA loading. Two gene expression assays, β-actin (ActB) and glyceraldehyde-3-phosphate dehydrogenase (Gapdh) (Table 1) were used as endogenous controls. Relative gene expression data generated by the RQ software for each of the two endogenous controls individually or the data normalised to the average of the two endogenous controls were imported into Microsoft Excel and analysed.

Statistical Analysis

Statistical analysis of normalised gene expression data before and after treatment was performed using two-tailed unpaired t tests (GraphPad Prism version 3.02 Software, San Diego, Calif., USA). Statistical significance was indicated by a P value≤0.05.

The aim of this study was to determine whether treatment with Rx-1 affected expression levels of genes involved in glucose uptake, insulin signalling, fatty acid oxidation, cytokine signalling and carbohydrate metabolism in the liver and muscle of OB/IR Wistar rats. The affect of Rx-1 treatment on the expression of genes involved in glucagon processing, insulin expression and transcription factors were analysed in the pancreas. Analysis of gene expression profiles after treatment may give insight into the mechanisms of action of Rx-1.

Gene expression levels in Rx-1 treated and control rats were normalised to ActB, Gapdh or the average of ActB and Gapdh. Although gene expression varied according to the endogenous control used, generally, Rx-1 treatment upregulated genes involved in glucose uptake (Glut1 and Glut2), insulin signalling (IR and IRS2), fatty acid oxidation (PPARα), cytokine signalling (SOCS3) and carbohydrate metabolism (GcgR) in the liver. Rx-1 treatment did not affect the expression of these genes in muscle samples. In the pancreas, Rx-1 treatment increased the expression of genes involved in glucagon processing, GLP-1R, Gcg and GcgR, the genes encoding insulin, Ins1 and Ins2 and the transcription factors Isl1 and Pdx1. None of the changes observed in the pancreas were statistically significant. The expression of Pcsk2 and nestin was unaffected by Rx-1 treatment. Neuro3 could not be detected in this study.

Rx-1 treatment increased Gck gene expression in the liver of OB/IR rats. However, the increase was not statistically significant. Gck is an enzyme predominantly expressed in the liver where it senses glucose and converts it to glucose-6-phosphate, the first step of glycolysis (Agius, 2008). A number of factors, including insulin (lynedjian et al. 1988) and phenolic compounds (Valentova et al. 2007) have been reported to upregulate Gck gene expression in the liver. Rx-1 treatment decreased Gck mRNA levels in muscle. It has previously been reported that muscle is not a major source of Gck activity.

This study showed increased expression of Glut1 and Glut2 in the liver of OB/IR Wistar rats treated with Rx-1. Glut4 mRNA levels in the muscle of these animals were unaffected by treatment. Glucose is important for cellular metabolism and the synthesis of ATP through glycolysis and the citric acid cycle. Facilitative glucose transport into cells is mediated by members of the GLUT protein family that belong to a much larger superfamily of 12 transmembrane segment transporters. At present, thirteen mammalian glucose transporter isoforms have been identified (Joost et al. 2002). These proteins are expressed in a tissue- and cell-specific manner.

GLUT1 is a widely expressed and mediates glucose transport into red cells and throughout the blood brain barrier, and provides most cells with their basal glucose requirement. It also plays a role in transporting glucose across epithelial and endothelial barrier tissues. Makni et al. (2008) reported that Glut1 polymorphisms are associated with T2D in the Tunisian population.

GLUT2 is a high-Km isoform expressed in hepatocytes, pancreatic beta cells, and the basolateral membranes of intestinal and renal epithelial cells. Single nucleotide polymorphisms (SNPs) in the Glut2 gene of Finnish subjects with impaired glucose tolerance were associated with a threefold risk for developing T2D (Laukkanen et al. 2005).

GLUT4 is expressed exclusively in the insulin-sensitive tissues, fat and muscle. It is responsible for increased glucose disposal in these tissues in the postprandial state and is important in whole-body glucose homeostasis. Insulin stimulation results in GLUT4 translocation from intracellular vesicles within a cell to the plasma membrane and increased glucose uptake. Failure of GLUT4 translocation results in insulin resistance and T2D. Glut4 gene expression and function is decreased during insulin resistance, T2D, obesity, and aging (Karnieli et al. 2008).

IR mRNA levels was increased in the liver of treated rats, whereas levels were unchanged in the muscle of these animals. The IR is a transmembrane protein that consists of an extracellular domain to which insulin binds and an intracellular domain with tyrosine kinase activity. Following insulin binding, the substrate tyrosine kinase activity of the IR initiates a cascade of cellular phosphorylation reactions where it phosphorylates a number of substrates including IRS1 and IRS2. These phosphorylated substrates then serve as docking molecules that bind to and activate cellular kinases, such as Pi3k, leading to glucose uptake, cell growth and protein synthesis (Youngren, 2007). Impaired IR function and signaling is associated with insulin resistance and T2D.

Rx-1 treatment increased IRS2 gene expression in the liver of treated rats. IRS1 mRNA levels were unchanged in the liver, while both IRS1 and IRS2 mRNA levels were unchanged in the muscle of these animals. Four isoforms of insulin receptor substrate (IRS) proteins have been identified (Thirone et al. 2006), with IRS1 and IRS2 being the most important. There are tissue-specific differences in the roles of the IRS proteins, with IRS1 playing a prominent role in skeletal muscle, while IRS2 is more important in the liver (White, 2002).

Pi3k was upregulated in the liver only. However, the upregulation was not significant. Pi3k plays a key role in insulin signalling and has been shown to be blunted in tissues of patients with T2D. A number of studies have provided evidence suggesting that insulin resistance, the main cause of T2D can potentially be treated by targeting Pi3k itself or its up and down-stream modulators (Jiang and Zhang, 2002).

PPARα was significantly upregulated in the liver after Rx-1 treatment. PPARα is predominantly expressed in the liver, and to a lesser extent in muscle, where it controls lipid metabolism and glucose homeostasis (Lefebvre et al. 2006). PPARα agonists have been used to treat obesity, insulin resistance and T2D. One of the mechanisms whereby PPARα improves insulin resistance is by upregulating the genes for fatty acid metabolism.

The expression of SOCS1 and SOCS3 mRNA was increased in the liver and muscle of Rx-1 treated rats. Only the upregulation of SOCS3 in the liver was statistically significant. SOCS1 and SOCS3 are two of a family of eight proteins that are thought to regulate cellular responses to cytokines in a negative feedback manner (Yasukawa et al. 2000). Studies have shown that SOCS1 and SOCS3 expression is increased in the liver of OB/IR mice (Ueki et al. 2005). Antisense-mediated knockdown of liver SOCS1 or 3 expression reverses insulin resistance in obese, diabetic mice, strongly supporting a role for SOCS proteins in obesity related insulin resistance (Ueki et al. 2005). The contradictory results obtained in this study highlights the complex gene networks involved in cytokine signalling, insulin resistance and T2D. The main function of the SOCS proteins are as negative regulators of cytokine signalling, therefore, increased expression of these genes may result in decreased cytokine signalling which is beneficial during insulin resistance and T2D (Krebs and Hilton, 2001).

Rx-1 treatment increased the expression of the GcgR gene in the liver and muscle after treatment. The upregulation of GcgR was not statistically significant. Charbonneau reported that high fat diet feeding of rats decreased total hepatic GcgR by about 55% (Charbonneau et al. 2007). Our data therefore suggests that Rx-1 treatment reverses the diet-induced downregulation of the GcgR.

GLP1R gene expression was increased in the pancreas after Rx-1 treatment. The incretin hormones, glucagon like peptide 1 (GLP1) and glucose-dependent insulinotropic peptide or also known as gastric inhibitory peptide (GIP) stimulate insulin release after the ingestion of carbohydrates and fats, maintaining glucose homeostasis (Kieffer and Habener, 1999). Disruption of the gene encoding the GLP1R results in glucose intolerance and the inability to secrete insulin in response to glucose (Scrocchi et al. 1996). Activation of the GLP1R induces β-cell neogenesis and proliferation (Xu et al. 1999), while inhibiting apoptosis (Li et al. 2003).

Rx-1 treatment increased Pdx1, Ins1 and Ins2 gene expression in the pancreas. Previous studies have reported that GLP1 treatment increases mRNA and protein levels of the transcription factor Pdx-1 (also known as IDX-1, STF1 and IUF1), and of insulin in the pancreas (Doyle and Egan, 2007). Other studies in our laboratory showed that circulating GLP1 levels were increased in the blood of Rx-1 treated OB/IR rats (Louw et al. 2008).

Since it has been shown that RX-1 can increase the expression of GLP-1 gene expression and the circulating plasma levels of GLP-1, it is possible that RX-1 acts by binding to one of the receptors associated with the regulation of incretin secretion. These are known as GPR 40, 43, 119, 120 and 131 (also known as TGR5) (e.g. Zhao Y F, Pei J, Chen C. J Endocrinol. 2008 September; 198(3):533-40. Epub 2008 Jun. 12. Activation of ATP-sensitive potassium channels in rat pancreatic beta-cells by linoleic acid through both intracellular metabolites and membrane receptor signalling pathway).

Cornish J, MacGibbon A, Lin J M, Watson M, Callon K E, Tong P C, Dunford J E, van der Does Y, Williams G A, Grey A B, Naot D, Reid I R. Modulation of osteoclastogenesis by fatty acids. Endocrinology. 2008 November; 149 (11):5688-95. Epub 2008 Jul. 10.

Robert M Jones†, James N Leonard, Daniel J Buzard & Juerg Lehmann GPR119 agonists for the treatment of type 2 diabetes Expert Opin. Ther. Patents (2009) 19(10)). Alternatively RX-1 could interact with molecules like the sodium-dependent glucose cotransporters (the SGLT family) (Gribble F M, Williams L, Simpson A K, Reimann F. Diabetes. 2003 May; 52(5):1147-54. A novel glucose-sensing mechanism contributing to glucagon-like peptide-1 secretion from the GLUTag cell line.) (O'Malley D, Reimann F, Simpson A K, Gribble F M. Diabetes. 2006 December; 55(12):3381-6. Sodium-coupled glucose cotransporters contribute to hypothalamic glucose sensing). (Krimi R B, Letteron P, Chedid P, Nazaret C, Ducroc R, Marie J C. Resistin-like molecule-beta inhibits SGLT-1 activity and enhances GLUT2-dependent jejunal glucose transport. Diabetes. 2009 September; 58(9):2032-8).

Pdx1 activates insulin gene expression by binding to its promoter and also prolongs the half-life of insulin mRNA (Poitout et al. 2006). In vitro and in vivo studies in rodents have shown that insulin gene expression is greatly reduced under circumstances of chronically elevated levels of glucose and fatty acids (Poitout et al. 2006). Insulin is encoded by the genes, insulin 1 (Ins1) and insulin 2 (Ins2). It is speculated that in rodents Ins1 arose from Ins2 due to an RNA mediated duplication-transposition process. Humans only have one insulin gene, with homology to the highly conserved rodent Ins2 (Madadi et al. 2008).

Gcg, the GcgR and Isl1 mRNA levels were increased in the pancreas of OB/IR rats after Rx-1 treatment. Glucagon is a hormone expressed in the liver where it stimulates glucose production. Isl1 has a critical role in the embryonic development of pancreatic endocrine cells (Ahlgren et al. 1997). In 2008, Koya et al. reported that treatment of streptozotocin-induced diabetic mice with recombinant Pdx-1 enhances β-cell regeneration and liver cell differentiation, restoring normoglycaemia. They further showed that Isl1 and Gcg mRNA levels in the liver and pancreas of these mice were upregulated after recombinant Pdx-1 treatment. Charbonneau et al. (2007) showed that total hepatic GcgR protein content was decreased in rats fed a high fat diet and that GcgR protein levels were increased slightly after exercise.

Nestin is a marker of pancreatic islet stem cells and it has been suggested that nestin-positive cells represent a multipotent pancreatic stem cell population, which could be used in future cell replacement therapies to cure diabetes (Lumelsky et al. 2001). In contrast, Delacour et al. (2004) showed that nestin is expressed in adult pancreatic exocrine cells, and suggests that nestin is not a specific marker of islet endocrine cells. In our study, nestin mRNA levels were unaffected by Rx-1 treatment.

Neurogenin 3 was not detected in the untreated or treated rats. Neurogenin-3 is a transcription factor expressed in endocrine progenitor cells and is required for endocrine-cell development in the pancreas (Habener et al. 2005). Lee et al. (2006) reported that Neurogenin-3 is not expressed in adult mouse pancreatic tissue. These results are in agreement with others (Dor et al. 2004) who have reported that replication of existing β-cells is the primary mechanism of β-cell regeneration in adult mice.

Pcsk2 or proconvertase 2 (PC2) mRNA levels were unaffected by Rx-1 treatment. In α-cells PC2 cleaves proglucagon to produce glucagon (Wideman et al. 2006).

In summary, this study showed upregulation of the genes involved in glucose uptake, insulin signalling, fatty acid metabolism and cytokine signalling in the liver of Rx-1 treated rats. The expression of genes encoding the hormones insulin and glucagon were increased in the pancreas of these rats, while the transcription factors Pdx1 and Isl1 were also upregulated. GcgR mRNA levels were increased in both the liver and pancreas of Rx-1 treated rats. Taken together, these results suggest that Rx-1 treatment may reverse insulin resistance and increase fatty acid oxidation in OB/IR rats.

Genes involved in glucose uptake (Glut1 and Glut2), insulin signalling (IR and IRS2), fatty acid oxidation (PPARα), cytokine signalling (SOCS1 and SOCS3) and the glucagon receptor were upregulated in the liver of Rx-1 treated rats. Only the glucagon receptor was upregulated in the muscle. The expression of the other genes was essentially unchanged. Genes involved in glucagon processing (GLP1R, Gcg and GcgR), insulin expression (Ins1 and Ins2) and the transcription factors (Isl1 and Pdx1) were upregulated in the pancreas of Rx-1 treated rats. The expression of Pcsk2 and nestin was unaffected by Rx-1 treatment, while neuro3 could not be detected.

Conclusion

Gene expression analysis is a useful technique that may give insight into the glucose-lowering mechanism of action of Rx-1. Results from this study suggest that Rx-1 acts in the liver where it stimulates glucose uptake, insulin signalling and fatty acid oxidation. In addition, Rx-1 seems to inhibit cytokine signalling, a hallmark of insulin resistance and type two diabetes. In the pancreas, Rx-1 treatment increased the expression of genes encoding insulin, the transcription factors, Isl1 and Pdx1, and GLP1R. Interestingly, GLP1 levels were also increased in the blood of these rats. Taken together, our results suggest that Rx-1 may reverse insulin resistance and increase glucose uptake and fatty acid oxidation in obese, insulin resistant rats.

Example 5

Glucose Uptake of RX-1 Analogues in a Transformed 3T3-L1 Adipocytes

The glucose uptake of RX-1 and selected analogues after administration of test compounds to Chang cell cultures were determined in an operating protocol for the 2-deoxy-[$^3$H]-D-glucose. The protocol, which is described in more detail below, has been designed to test for the RX-1 (and RX-1 analogues) mediated glucose uptake. In Table the EC50 values for the uptake for RX-1 and representative analogues is shown.

TABLE 2

| Compound | EC50 (micromolar) |
|---|---|
| RX-1 | 3.224 |
| RX-2 | 9.353 |
| RX-4 | 80.77 |
| RX-5 | 114.2 |
| RX-10 | 105.1 |
| RX-16 | 6.986 |
| RX-18 | 9.5 |
| RX-19 | 180.7 |
| RX-20 | 5.7 |
| RX-21 | 285.7 |

Compound Handling

RX-1 and RX-1 analogues in powder form are stored at RT (20-24° C.) under vacuum desiccation in the dark.

Stock Solutions

RX-1 Stock Solution (1.0 mM).

The RX-1 stock solution is made fresh for each assay run. For a 1.0 mM RX-1 stock solution, 3.3 mg of RX-1 is dissolved in 10 ml DMEM (without phenol red, glucose L-Glutamine and pyruvate) supplemented with 0.1% BSA.

RX-1 Analogue Stock Solutions (5 or 4 mM)

Stock solutions of the RX-1 analogues supplied in cryo vials (DrugMode) was prepared by diluting the compound with 200 sterile tissue culture grade water. This will yield a 5 mM stock solution. If the analogue does dissolve completely an additional 50 µl methanol will be added (this will be recorded clearly on the log sheet). This will yield a 4 mM stock solution. Stock solutions will be kept on ice at all times and analogues will be stored in 20 µl aliquots at −80 C for subsequent use. Tubes that have been thawed will be clearly marked on the label.

Working Solutions

RX-1 (10 µM) Positive Control Solution

To prepare a 10 µM RX-1 solution as positive control.
  Add 30 µl to 2970 µl modified DMEM media supplemented with 8 mM glucose.

RX-1 Analogue (31.6 µM) Test Solutions

To prepare a 31.6 µM RX-1 analogue test solution. Add 19 µl of the 5 mM to 2981 µl modified DMEM media supplemented with 8 mM glucose. To prepare a 31.6 µM RX-1 analogue test solution from a 4 mM stock solution, add 24 µl to 2976 µl modified DMEM media supplemented with 8 mM glucose.

Cell Seeding in 24-Well Plates

Chang cells are cultured according to procedures described in MRC cell culture SOPs: TC-B2a Thawing of cells and TC-B1a Cell line maintenance—general principles. Make sure cells are in the log phase (i.e. <70% confluence) and less than 20 passages.

Harvest cells using 0.25% (w/v) Trypsin/0.53 mM EDTA solution.

Count cells and resuspend to 30 000 cells/ml (Chang cell seeding density for 24-well plate=30 000 cells/ml) in EMEM (with pyruvate and NEAA, but without L-glutamate (Lonza, USA) containing 10% FBS (Gibco, UK) and pipette 1 ml/well cell suspension to a 24-well plate corresponding to 30 000 cells/well.

2-deoxy-[$^3$H]-D-glucose Uptake Assay after 3 days of cell growth, aspirate medium
wash cells once with pre-warmed DPBS at 37° C.
add 500 µl of pre-warmed 37° C. DMEM/0.1% BSA (without phenol red, glucose and pyruvate) to serum starve cells to remove residual glucose and FBS
incubate at 37° C. in humidified air and 5% CO$_2$ for 30 min
aspirate DMEM/0.1% BSA (without phenol red, glucose and pyruvate)
Prepare test dilutions as specified in the plate layout (see below)
add 500 µl pre-warmed 37° C. of test dilution per well according to plate layout
incubate at 37° C. in humidified air and 5% CO$_2$ for 3 hrs
remove test medium and wash cells once with DPBS (37° C.)
add 250 µl of test medium containing 0.5 µCi/ml $^3$H-2-DOG to each well use (0.5 µl $^3$H to 1 ml medium)
Incubate cells at 37° C. in humidified air and 5% CO$_2$ for 15 min
Aspirate medium
To stop the reaction, wash cells twice with ice-cold DPBS
Aspirate DPBS and ensure that wells are as dry as possible
Lyse cells by adding 1 ml of 0.3N NaOH/1% SDS and incubate at 37° C. for at least 45 min
Mix cell lysate thoroughly before subsequent use in LSC and Bradford protein determination

The invention claimed is:

1. Compound of formula I or a physiologically acceptable salts thereof:

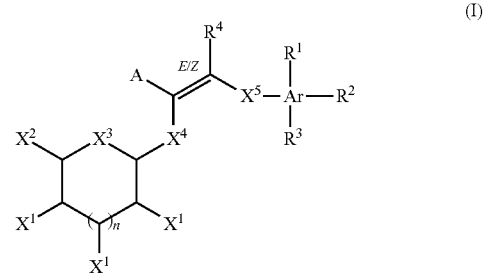

wherein,
  Ar is benzene;
  n is 1;
  $R^1$, $R^2$, $R^3$, and $R^4$ are independently selected from the group consisting of hydrogen, fluorine, chlorine, bromine, iodine, aryl, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperizin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano, and nitro, $X^1$ is independently selected from the group consisting of —OH, H, —OR$^5$, and —OC(O)R$^5$;

$X^2$ is selected from the group consisting of CH2OH, and —CH$_2$OR$^5$;

$X^3$ is —O—;

$X^4$ is —O—;

$X^5$=(—CH$_2$)$_m$—;

m is 0, 1, 2 or 3;

A is selected from the group consisting of —CO$_2$H, —CO$_2$R$^5$, —SO$_3$H; —SO$_2$HNR$^5$; —PO(OH)$_2$; —CONH(CO)R$^5$; —CONH(CO)H, —CONHSO$_2$R$^5$; —CONHCN; and

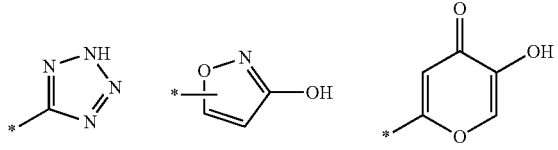

where the bond marked * is attached to the ethylene; and $R^5$ is selected form group consisting of $C_1$-$C_6$ straight or branched chain alkyl, $C_2$-$C_6$ straight or branched chain alkenyl or alkynyl, aryl, aralkyl, heteroaryl, carbocycle, and heterocycle;

with the proviso that:

If $R^1$, $R^2$, $R^3$, and $R^4$ are —H, A is not —CO$_2$H or —CO$_2$R$^5$, when $X^1$ is OH, $X^3$ and $X^4$ is —O—, n is 1, and $X^5$ is (—CH$_2$)$_m$—, where m is 0; and $R^1$, $R^2$ or $R^3$ is not in para position relative to $X^5$ if $R^1$, $R^2$ or $R^3$ is selected from $C_{1-6}$-alkyloxy, $C_{3-10}$-cycloalkyloxy, $C_{5-10}$-cycloalkenyloxy, aryloxy, and hydroxy.

* * * * *